United States Patent
Holbein et al.

(10) Patent No.: US 11,059,785 B2
(45) Date of Patent: Jul. 13, 2021

(54) POLYMERIC METAL CHELATING COMPOSITIONS AND METHODS OF PREPARING SAME FOR CONTROLLING GROWTH AND ACTIVITIES OF LIVING CELLS AND ORGANISMS

(71) Applicant: CHELATION PARTNERS INCORPORATED, Guelph (CA)

(72) Inventors: Bruce E. Holbein, Guelph (CA); M. Trisha C. Ang, Scarborough (CA); Dnyaneshwar Vithoba Palaskar, Pule (IN); Ganugapati Satyanarayana, Bangalore (IN); Gireesh Mahandru, Saket (IN); S. Vijaya Bhaskara Reddy, District Prakasham (IN); Sazid Ali, Akbarpur (IN)

(73) Assignee: CHELATION PARTNERS INCORPORATED, Ontario (CA)

( * ) Notice: Subject to any disclaimer, the term of this patent is extended or adjusted under 35 U.S.C. 154(b) by 0 days.

(21) Appl. No.: 16/327,694

(22) PCT Filed: Aug. 25, 2017

(86) PCT No.: PCT/CA2017/050999
§ 371 (c)(1),
(2) Date: Feb. 22, 2019

(87) PCT Pub. No.: WO2018/035613
PCT Pub. Date: Mar. 1, 2018

(65) Prior Publication Data
US 2019/0169126 A1 Jun. 6, 2019

Related U.S. Application Data

(60) Provisional application No. 62/380,047, filed on Aug. 26, 2016.

(51) Int. Cl.
| | |
|---|---|
| C07D 213/69 | (2006.01) |
| A61K 31/787 | (2006.01) |
| C08F 220/60 | (2006.01) |
| A61P 39/04 | (2006.01) |
| C08F 220/54 | (2006.01) |
| C08F 226/10 | (2006.01) |

(52) U.S. Cl.
CPC .......... *C07D 213/69* (2013.01); *A61K 31/787* (2013.01); *A61P 39/04* (2018.01); *C08F 220/54* (2013.01); *C08F 220/60* (2013.01); *C08F 226/10* (2013.01); *C08F 2438/03* (2013.01)

(58) Field of Classification Search
CPC .................................................. C07D 213/69
See application file for complete search history.

(56) References Cited

U.S. PATENT DOCUMENTS

| 8,454,934 B2 | 6/2013 | Scott et al. |
| 2016/0038604 A1 | 2/2016 | Holbein et al. |

FOREIGN PATENT DOCUMENTS

| WO | 2007140059 A2 | 12/2007 | |
| WO | WO2007/140059 | * 12/2007 | .............. C08G 63/91 |
| WO | 2012167368 A1 | 12/2012 | |
| WO | WO2012/167368 | * 12/2012 | ................ C02F 1/28 |

OTHER PUBLICATIONS

Cinelli, M., et al., "Synthesis and biologicial evaluation of 14-(aminoalkyl-aminomethyl)-aromathecins as topoisomerase I inhibitors: Investigating the hypothesis of shared structure-activity relationships", Bioorg. Med. Chem., 2009 17(20), 7145-7155.
Holbein, B., et al., "Effect of trace iron levels and iron withdrawal by chelation on the growth of Candida albicans and Cadida vini", FEMS Microbiol Lett. 307 pp. 19-24 (2010).
Jarowicki, K., et al., "Protecting groups", Contemp. Org. Synth. 1997, 4, 454-492.
Keddie, D., et al., "RAFT Agent Desing and Synthesis", Marcomolecules, 2012, 45, 5321-5342.
Zelikin, A., et al., "Poly(vinylpyrrolidone) for Bioconjugation and Surface Ligand Immobilization", Biomarcomolecules, 2007, 8, 2950-2953.
International Search Report for International Application No. PCT/CA2017/050999 dated Nov. 9, 2017 (3 pages).
International Preliminary Report on Patentability and Written Opinion of the International Searching Authority for International Application No. PCT/CA2017/050999 Nov. 9, 2017 (6 pages).
Ang et al, Med. Chem. Commun., 2018, 9, 1206-1212, "DIBI, a 3-hydroxypyridin-4-one chelator iron binding polymer with enhanced antimicrobial activity".
Parquet et al, Frontiers in Microbiology 9:1811, "Novel Iron-Chelator DIBI Inhibits *Staphylococcus aureus* Growth, Suppresses Experimental MRSA Infection in Mice and Enhances the Activities of Diverse Antibiotics in vitro".
Parquet et al, 2019, Antimicrob Agents Chemother 63:e00855-19. "Antibiotic-resistant Acinetobacter baumannii is susceptible to the novel iron sequestering anti-infective DIBI in vitro and in experimental pneumonia in mice".

\* cited by examiner

*Primary Examiner* — Paul V Ward
(74) *Attorney, Agent, or Firm* — Venable LLP

(57) ABSTRACT

Disclosed are chelating co-polymer compositions that are soluble in aqueous media and chelate essential metals, methods of preparation and uses thereof. The chelating compositions are comprised of two or more different monomers, at least one of which possesses metal binding or metal chelating activity. The chelating compositions are synthesized by reversible addition-fragmentation transfer (RAFT) polymerization with the aid of a suitable RAFT-mediating agent. Also described are chelating compositions that comprise hydroxypyridinone chelating groups. The ability of the chelating compositions to bind metals affects the activity of a living cells and organisms, which require the metals for cellular functions.

18 Claims, 15 Drawing Sheets

PRIOR ART

PRIOR ART

PRIOR ART

RAFT-3

RAFT-4

RAFT-5

MAHMP-Acrylamide co-polymer

MAHMP-Pyrrolidone co-polymer

FRP prepared MAHMP-NVP co-polymer

RAFT prepared MAHMP-NVP co-polymer

FRP prepared MAHMP-NVP co-polymer

RAFT prepared MAHMP-NVP co-polymer

POLYMERIC METAL CHELATING COMPOSITIONS AND METHODS OF PREPARING SAME FOR CONTROLLING GROWTH AND ACTIVITIES OF LIVING CELLS AND ORGANISMS

The present application is a national-stage entry under 35 U.S.C. § 371 of International Patent Application No. PCT/CA2017/050999, published as WO 2018/035613 A1, which International Application claims benefit to U.S. Provisional Application Ser. No. 62/380,047, filed Aug. 26, 2016, the entire disclosure of each of which is incorporated by reference herein.

FIELD OF THE INVENTION

The present invention relates to metal chelating polymer compositions that are soluble in aqueous media. The present invention also relates to metal chelating compositions that sequester iron and prevent, inhibit or reduce the uptake of iron in cells that are being targeted.

BACKGROUND

Iron is required and cannot be replaced by other metals for many essential aspects of a living cell's physiology and metabolism, whether the cell is a spoilage-causing microbe in a product intended for use by humans or a pathogenic cell, such as a microbial pathogen (bacterial, fungal or parasitic) or a pathogenic animal cancer cell within the body and capable of causing disease in an animal, including a human and a fish. The only known exception to this essential requirement for iron is with certain non-pathogenic Lactobacilli bacteria.

This generally universal iron requirement could therefore be a useful target for new means to interfere with or stop the growth of cells. To date, only limited advances have been made in affecting iron nutrition of cells due to a lack of suitable chemical compounds that possess the needed characteristics. Bacterial, fungal, parasitic and animal cells normally possess one or more of various iron uptake mechanisms that operate at the cell membrane/external environment boundary and these cellular mechanisms essentially serve to internalize iron from the external environment for use within the cell.

Iron reduction at/by a surface receptor/reduction/transport system is important for making iron that predominates in aerobic environments as insoluble $Fe^{3+}$ into the more soluble $Fe^{2+}$ form, and this mechanism is found in most bacterial, fungal and animal cells. Pathogenic bacteria and yeasts generally possess multiple iron uptake mechanisms while animal cells do not produce or utilize microbial type siderophores. Siderophores are chelating compounds produced primarily by microbial cells. Rather than using a siderophore, vertebrate animal cells utilize the protein transferrin that is typically produced by liver cells of the animal and which circulates to shuttle iron from the gut through the blood stream and to all other cells of the body. Certain pathogenic microorganisms have developed an ability to bind and utilize transferrin Fe by transferring this to a shuttle carrier in the membrane without taking up the transferrin molecule into the cell. Other bacteria and fungi can take up heme, another iron-carrying compound produced by microbial and animal cells. Heme can be taken into the cell by some pathogenic microorganisms directly by a receptor/transport system and the cells then use the heme iron internally. Various bacteria and fungi can utilize various heterologous siderophores produced by other microbes by removing iron from these at the cell surface shuttle system. The iron reduction mechanism may potentially play a role in iron removal from heterologous siderophores or transferrin in some cells. Various bacterial and fungal pathogens produce their own autologous siderophores in response to iron need, secrete these into the extracellular environment and then take these back up with iron as chelated from the external environment. Cells of parasitic animals have been studied less but some are known to acquire heme and it is likely that they employ acquisition mechanisms similar to other eukaryotic cells such as fungi or animal cells.

Metal chelating co-polymer compositions that are soluble in aqueous media have been previously disclosed in US patent application publication No. US2016/0038604 A1 (hereby incorporated by reference), wherein the compositions described therein are suitable for chelating one or more essential metals and optionally trace metals. The chelating compositions described therein are soluble in aqueous media and are comprised of one or more suitable metal binding chemical groups, including wherein the metal binding chemical group is a portion of a monomer group comprising a metal binding first monomer unit, which is mixed with a second monomer group to polymerize the two monomer groups so that the resulting co-polymer remains soluble in aqueous solution and has metal chelating activity. US patent application publication No. US2016/0038604 A1 further discloses that for the compositions outlined above, preferred embodiments include compositions where the metal binding first monomer unit is 3-hydroxy-1-(β-methacrylamidoethyl)-2-methyl-4(1H)-pyridinone (MAHMP), the second monomer is either 1-vinyl-2-pyrrolidone or N,N-dimethylacrylamide and the final chelating composition is a linear soluble co-polymer of the first and second monomer groups.

However, co-polymerization of the first and second monomers as described above presents unanticipated issues. These issues are in part in relation to the incomplete utilization of the monomers in the polymerization reaction, wherein unreacted amounts of the monomers, especially the first metal binding monomer MAHMP, may remain. Furthermore, the polymerization of the previously disclosed composition produced a wide range of molecular weight compositions in the same reaction.

The use of the chelating compositions having a narrower distribution of weight in an animal would be generally beneficial. The use of polymeric metal binding compositions especially if for medical applications as on or within the bodies of an animal would benefit from, or in certain applications may require, a particular preferred size range of the polymeric composition. For example, a relatively high molecular weight composition may be more useful for a topical application to the skin or other body surface area to help retain the composition at or near the application site, whereas a relatively low molecular weight composition may be useful for systemic use within the body so as to allow better systemic distribution and eventual clearance of the composition from the body.

It would be desirable to obtain more effective and complete utilization of the monomer units during the polymerization to produce the final chelating compositions. It would also be desirable to obtain more effective control over the molecular weight of the chelating compositions and especially a greater uniformity of the population of chelating composition molecules.

SUMMARY OF THE INVENTION

Chelating co-polymer compositions that are soluble in aqueous media and chelate essential metals are provided together with methods for their preparation and uses thereof. The chelating compositions may be prepared from two or more different monomers, at least one of which possesses metal binding or metal chelating activity. The chelating compositions may be synthesized by reversible addition-fragmentation transfer (RAFT) polymerization with the aid of a suitable RAFT-mediating agent. Chelating compositions are also described herein that comprise hydroxypyridinone metal binding groups, wherein, in certain embodiments, the hydroxypyridinone may optionally be 3-hydroxy-1-(8-methacrylamidoethyl)-2-methyl-4(1H)-pyridinone. The ability of chelating compositions to bind metals may be leveraged to affect the activity of a living cell and/or organism, which require these metals for cellular functions.

According to an aspect of the present invention, there is provided a chelating composition soluble in aqueous media with chelating activity for an essential metal, the chelating composition prepared from:

at least a first and a second monomer unit, wherein the first monomer unit comprises one or more suitable metal binding chemical groups incorporated or affixed thereto; wherein:

the first and second monomer units are polymerized by a reversible addition-fragmentation chain transfer mechanism with the use of a suitable addition-fragmentation chain transfer agent; and the resulting chelating composition binds one or more essential metal in the environment of a living cell or organism and thereby affects the living cell or organism.

In a further embodiment of the chelating composition outlined above, the one or more suitable metal binding chemical groups are independently selected from the group consisting of the carboxyl, hydroxyl, phenolate, catecholate, hydroxamate, hydroxypyridinone and hydroxyphenyltriazole chemical types.

In a further embodiment of the chelating composition or compositions outlined above, the one or more suitable metal binding chemical groups are the hydroxypyridinone chemical type

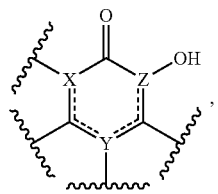

wherein X, Y and Z are independently N or C such that:
when X is N, Y and Z are C,
when Y is N, X and Z are C, and
when Z is N, X and Y are C.

In a further embodiment of the chelating composition or compositions outlined above, the first monomer unit is represented by Compound (I)

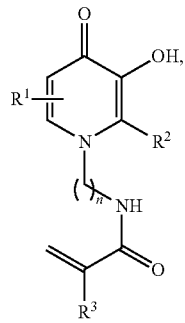

Compound (I)

wherein
$R^1$ is independently selected from the group consisting of H, alkyl and alkyl substituted with O, N or S;
$R^2$ is independently selected from the group consisting of H, alkyl and alkyl substituted with O, N or S;
$R^3$ is independently selected from the group consisting of H, alkyl and alkyl substituted with O, N or S; and
n is 1 to 12.

In a further embodiment of the chelating composition or compositions outlined above, Compound (I) is prepared by polymerizing Compound (Ia)

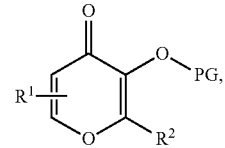

Compound (Ia)

wherein
$R^1$ is independently selected from the group consisting of H, alkyl and alkyl substituted with O, N or S;
$R^2$ is independently selected from the group consisting of H, alkyl and alkyl substituted with O, N or S; and
PG is a protecting group,
with Compound (Ib)

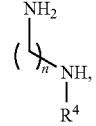

Compound (Ib)

wherein
n is 1 to 12; and
$R^4$ is $COCCH_2R^3$ or a protecting group,
followed by:
when $R^4$ is $COCCH_2R^3$, removing PG to yield Compound (I); or
when $R^4$ is a protecting group, removing $R^4$, reacting with a suitable acrylate source, and removing PG to yield Compound (I).

In a further embodiment of the chelating composition or compositions outlined above, when $R^4$ is $COCCH_2R^3$, Compound (Ib) is prepared by reacting a suitable acrylate source with an alkanediyl diamine.

In a further embodiment of the chelating composition or compositions outlined above, PG is a benzyl ether protecting group.

In a further embodiment of the chelating composition or compositions outlined above, when $R^4$ is a protecting group, the protecting group is a tert-butyloxycarbonyl protecting group.

In a further embodiment of the chelating composition or compositions outlined above,
$R^1$ is H;
$R^2$ is methyl;
$R^3$ is methyl; and
n is 1 to 6.

In a further embodiment of the chelating composition or compositions outlined above, the first monomer unit is represented by Compound (II)

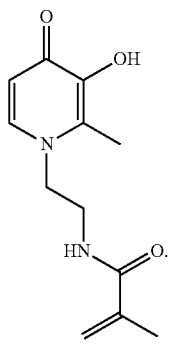

Compound (II)

In a further embodiment of the chelating composition or compositions outlined above, the second monomer unit is independently selected from the group consisting of 1-vinyl-2-pyrrolidone, acrylic acid, methyl methacrylate, N,N-dimethyl-acrylamide, ethyl methacrylate, N-vinyl imidazole and styrene.

In a further embodiment of the chelating composition or compositions outlined above, the second monomer unit is 1-vinyl-2-pyrrolidone.

In a further embodiment of the chelating composition or compositions outlined above, the second monomer unit is N,N-dimethyl-acrylamide.

In a further embodiment of the chelating composition or compositions outlined above, the suitable addition-fragmentation chain transfer agent is independently selected from the group consisting of 2-ethoxythiocarbonylsulfanyl-propionic acid ethyl ester and 2-ethoxythiocarbonyl sulfanyl-2-methyl-propionic acid.

In a further embodiment of the chelating composition or compositions outlined above, a residue of the addition-fragmentation chain transfer agent is removed in whole or in part from the chelating composition after polymerization.

In a further embodiment of the chelating composition or compositions outlined above, the chelating composition comprises one or more different structural architectures independently selected from the group consisting of alternating, periodic, diblock, triblock and multiblock and comprise one or more forms independently selected from the group consisting of linear, branched, brush, comb and star.

In a further embodiment of the chelating composition or compositions outlined above, the chelating composition has a lower molecular weight limit of around 1500 Daltons and has no upper molecular weight limit provided it remains soluble in aqueous media prior to the binding of the metal.

In a further embodiment of the chelating composition or compositions outlined above, the essential metal is an essential transition series metal.

In a further embodiment of the chelating composition or compositions outlined above, the essential metal is iron, manganese, copper, cobalt, magnesium or nickel.

In a further embodiment of the chelating compositions or compositions outlined above, the essential metal is iron.

In a further embodiment of the chelating composition or compositions outlined above, the living cell or organism is affected in its growth or activities by having insufficient amounts of the essential metal available for its use.

According to an aspect of the present invention, there is provided a use of the chelating composition or compositions outlined above for the treatment of a disease in an animal, including a fish or a human, wherein the disease is caused by a cell or cells, or the activity of the cell or cells, wherein the cell or cells causing the disease are one or more of a microbial cell, a cancer cell or a uni-cellular or multi-cellular parasitic organism.

According to an aspect of the present invention, there is provided a use of the chelating composition or compositions outlined above for the manufacture of a medicament for the treatment of a disease in an animal, including a fish or a human, wherein the disease is caused by a cell or cells, or the activity of the cell or cells, wherein the cell or cells causing the disease are one or more of a microbial cell, a cancer cell or a uni-cellular or multi-cellular parasitic organism.

In a further embodiment of the uses outlined above, the chelating composition is for administration to the animal.

In a further embodiment of the uses outlined above, the chelating composition is for administration in conjunction with an anti-cellular agent, wherein the anti-cellular agent is one or more of an anti-microbial agent, an anti-metabolite agent, an anti-viral agent, an anti-parasitic agent or an anti-cancer agent.

According to an aspect of the present invention, there is provided a method of treating a disease in an animal, including a fish or a human, by administrating a therapeutically effective amount of the chelating composition outlined above, wherein the disease is caused by a cell or cells, or the activity of the cell or cells, wherein the cell or cells causing the disease are one or more of a microbial cell, a cancer cell or a uni-cellular or multi-cellular parasitic organism.

In a further embodiment of the method outlined above, the chelating composition is administrated in conjunction with an anti-cellular agent, wherein the anti-cellular agent is one or more of an anti-microbial agent, an anti-metabolite agent, an anti-viral agent, an anti-parasitic agent or an anti-cancer agent.

According to an aspect of the present invention, there is provided a pharmaceutical composition comprising the chelating composition outlined above and a pharmaceutically acceptable carrier.

According to an aspect of the present invention, there is provided a pharmaceutical composition comprising the chelating composition outlined above and an anti-cellular agent and/or an anti-microbial preservative agent.

According to an aspect of the present invention, there is provided a metal binding compound represented by Compound (I),

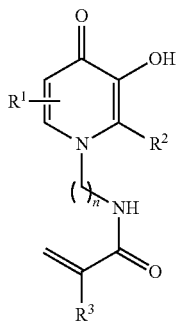

Compound (I)

wherein:
R¹ is independently selected from the group consisting of H, alkyl and alkyl substituted with O, N or S;
R² is independently selected from the group consisting of H, alkyl and alkyl substituted with O, N or S;
R³ is independently selected from the group consisting of H, alkyl and alkyl substituted with O, N or S; and
n is 1 to 12,
wherein Compound (I) is prepared by polymerizing Compound (Ia)

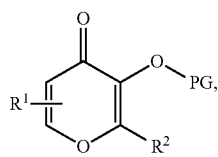

Compound (Ia)

wherein
R¹ is independently selected from the group consisting of H, alkyl and alkyl substituted with O, N or S;
R² is independently selected from the group consisting of H, alkyl and alkyl substituted with O, N or S; and
PG is a protecting group,
with Compound (Ib)

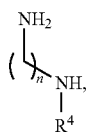

Compound (Ib)

wherein
n is 1 to 12; and
R⁴ is COCCH₂R³ or a protecting group, by a reversible addition-fragmentation chain transfer mechanism with the use of a suitable addition-fragmentation chain transfer agent followed by:
when R⁴ is COCCH₂R³, removing PG to yield Compound (I); or
when R⁴ is a protecting group, removing R⁴, reacting with a suitable acrylate source, and removing PG to yield Compound (I), and
wherein Compound (I) binds one or more essential metal.
In a further embodiment of the metal binding compound outlined above, R¹ is H;
R² is methyl;
R³ is methyl; and
n is 1 to 6.

In a further embodiment of the chelating composition or compositions outlined above, the first monomer unit is represented by Compound (III)

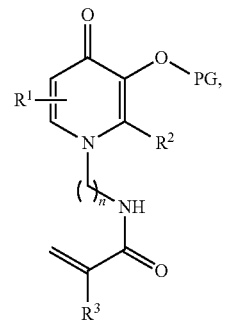

Compound (III)

wherein
R¹ is independently selected from the group consisting of H, alkyl and alkyl substituted with O, N or S;
R² is independently selected from the group consisting of H, alkyl and alkyl substituted with O, N or S;
R³ is independently selected from the group consisting of H, alkyl and alkyl substituted with O, N or S;
n is 1 to 12; and
PG is a protecting group.

In a further embodiment of the chelating composition outlined above, PG is removed by suitable means after polymerization.

According to an aspect of the present invention, there is provided a method of preparing a chelating composition soluble in aqueous media with chelating activity for an essential metal, the method comprising:
providing a first monomer unit comprising one or more suitable metal binding chemical groups incorporated or affixed thereto; and
polymerizing the first monomer unit with at least a second monomer unit by a reversible addition fragmentation chain transfer mechanism with the use of a suitable addition fragmentation chain transfer agent,
wherein the chelating composition binds one or more essential metal in the environment of a living cell or organism and thereby affects the living cell or organism.

In a further embodiment of the method outlined above, the one or more suitable metal binding chemical groups are independently selected from the group consisting of carboxyl, hydroxyl, phenolate, catecholate, hydroxamate, hydroxypyridinone and hydroxyphenyltriazole chemical types.

In a further embodiment of the method outlined above, the one or more suitable metal binding chemical groups are the hydroxypyridinone chemical type

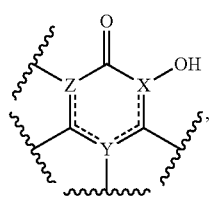

wherein X, Y and Z are independently N or C such that:
when X is N, Y and Z are C,
when Y is N, X and Z are C, and
when Z is N, X and Y are C.

In a further embodiment of the method or methods outlined above, wherein the first monomer unit is represented by Compound (I)

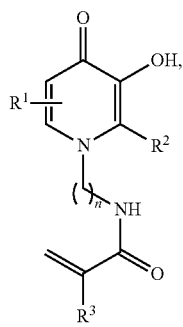

Compound (I)

wherein
- $R^1$ is independently selected from the group consisting of H, alkyl and alkyl substituted with O, N or S;
- $R^2$ is independently selected from the group consisting of H, alkyl and alkyl substituted with O, N or S;
- $R^3$ is independently selected from the group consisting of H, alkyl and alkyl substituted with O, N or S; and
- n is 1 to 12.

In a further embodiment of the method or methods outlined above, Compound (I) is prepared by polymerizing Compound (Ia)

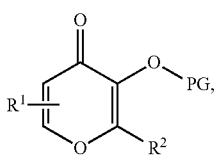

Compound (Ia)

wherein
- $R^1$ is independently selected from the group consisting of H, alkyl and alkyl substituted with O, N or S;
- $R^2$ is independently selected from the group consisting of H, alkyl and alkyl substituted with O, N or S; and
- PG is a protecting group, with Compound (Ib)

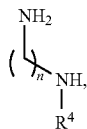

Compound (Ib)

wherein
n is 1 to 12; and
$R^4$ is $COCCH_2R^3$ or a protecting group,
followed by:
when $R^4$ is $COCCH_2R^3$, removing PG to yield Compound (I); or
when $R^4$ is a protecting group, removing $R^4$, reacting with a suitable acrylate source, and removing PG to yield Compound (I).

In a further embodiment of the method or methods outlined above, when $R^4$ is $COCCH_2R^3$, Compound (Ib) is prepared by reacting a suitable acrylate source with an alkanediyl diamine.

In a further embodiment of the method or methods outlined above, PG is a benzyl ether protecting group.

In a further embodiment of the method or methods outlined above, when $R^4$ is a protecting group and wherein the protecting group is a tert-butyloxycarbonyl protecting group.

In a further embodiment of the method or methods outlined above,
$R^1$ is H;
$R^2$ is methyl;
$R^3$ is methyl; and
n is 1 to 6.

In a further embodiment of the method or methods outlined above, the first monomer unit is represented by Compound (II)

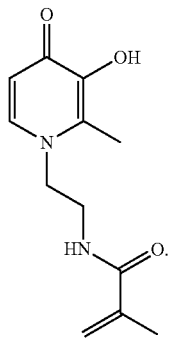

Compound (II)

In a further embodiment of the method or methods outlined above, the second monomer unit is independently selected from the group consisting of 1-vinyl-2-pyrrolidone, acrylic acid, methyl methacrylate, N,N-dimethyl-acrylamide, ethyl methacrylate, N-vinyl imidazole and styrene.

In a further embodiment of the method or methods outlined above, the second monomer unit is 1-vinyl-2-pyrrolidone.

In a further embodiment of the method or methods outlined above, the second monomer unit is N,N-dimethyl-acrylamide.

In a further embodiment of the method or methods outlined above, the suitable addition-fragmentation chain transfer agent is independently selected from the group consisting of 2-ethoxythiocarbonylsulfanyl-propionic acid ethyl ester and 2-ethoxythiocarbonyl sulfanyl-2-methyl-propionic acid.

In a further embodiment of the method or methods outlined above, a residue of the addition-fragmentation chain transfer agent is removed in whole or in part from the chelating composition after polymerization.

In a further embodiment of the method or methods outlined above, the first monomer unit is represented by Compound (III)

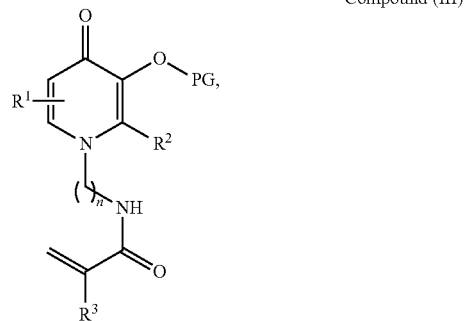

Compound (III)

wherein
- $R^1$ is independently selected from the group consisting of H and $C_{1-3}$alkyl;
- $R^2$ is independently selected from the group consisting of H and $C_{1-3}$alkyl;
- $R^3$ is independently selected from the group consisting of H, $C_{1-3}$alkyl and $C_{1-3}$alkyl substituted with O or N;
- n is 1 to 12; and
- PG is a protecting group.

In a further embodiment of the method outlined above, PG is removed by suitable means after polymerization.

In a further embodiment of the compositions, compounds and methods outlined above, n is at least 2.

DETAILED DESCRIPTION

Figure 1:
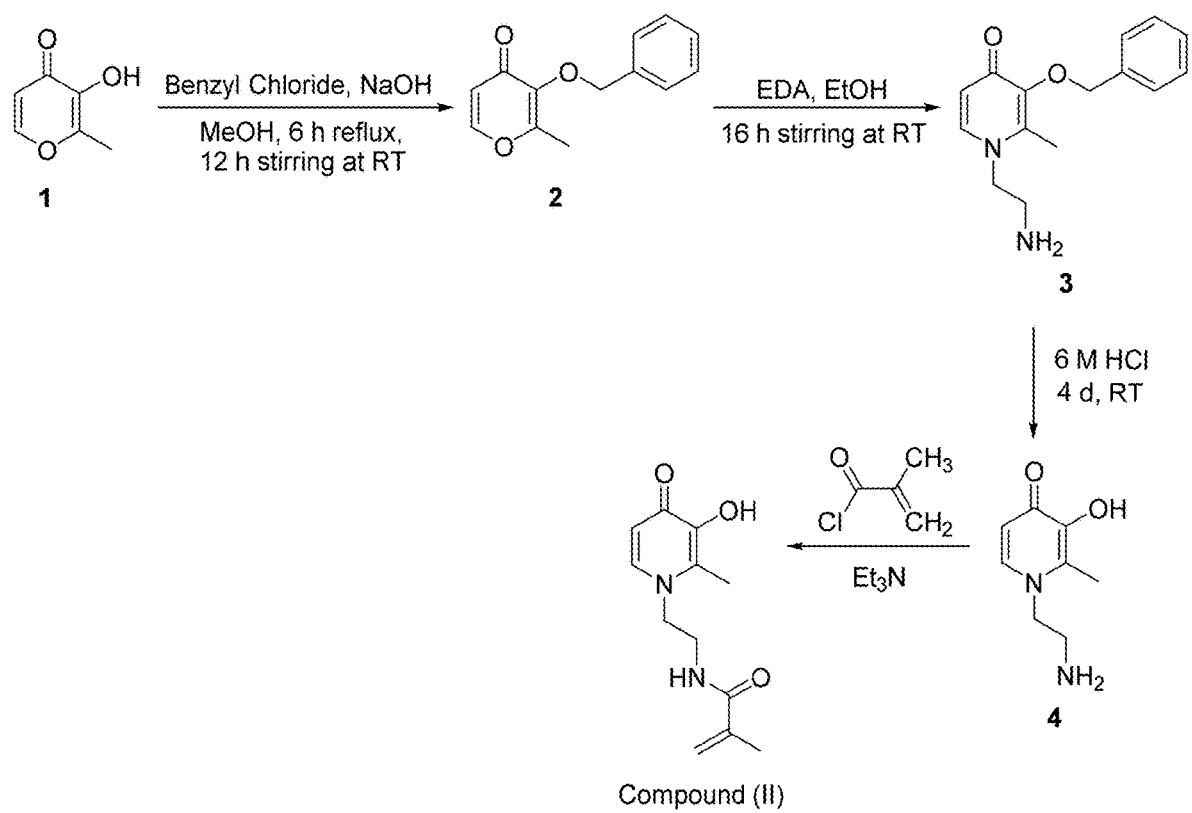
FIG. 1 (prior art) shows the overall chemical synthesis sequence for the conventional synthesis of 3-hydroxy-1-(β-methacrylamidoethyl)-2-methyl-4(1H)-pyridinone (MAHMP, Compound (II)) chelating monomer useful for preparation of chelating compositions through preparation of the key intermediate 1-aminoethyl-3-hydroxy-2-methyl-4(1H)-pyridinone (AHMP) as detailed in Example 1.

Described herein are embodiments illustrative of chelating compositions soluble in aqueous media or organic media, methods of their preparation and uses thereof. It will be appreciated that the embodiments and examples described herein are for illustrative purposes intended for those skilled in the art and are not meant to be limiting in any way. All references to embodiments or examples throughout the disclosure should be considered a reference to an illustrative and non-limiting embodiment or an illustrative and non-limiting example.

According to an embodiment of the present invention, there is provided a composition that is soluble in aqueous or organic media possessing chelating activity for an essential metal.

According to an embodiment of the present invention, there is provided a method of preparing a composition that is soluble in aqueous or organic media possessing chelating activity for an essential metal.

In the context of the present invention, chelating activity for an essential metal encompasses the ability to sequester transition metals, including iron. This also may encompass the ability to prevent the uptake of the transition metals by the cells that are being targeted when the transition metals are being sequestered by the chelating composition. In this regard, the chelating compositions can chelate iron and/or other essential metals in the environment of a living cell or organism, such that the chelated metal is potentially no longer readily accessible to the normal metal acquisition mechanisms of the cell or organism.

The present invention provides for a chelating composition soluble in aqueous media with chelating activity for an essential metal prepared from at least a first and a second monomer unit, wherein the first monomer unit comprises one or more suitable metal binding chemical groups incorporated or affixed thereto. The first and second monomer units are polymerized by a reversible addition-fragmentation chain transfer (RAFT) mechanism with the use of a suitable addition-fragmentation chain transfer agent. The resulting polymer composition is referred to as co-polymer composition.

The present invention also provides for a method of preparing a chelating composition soluble in aqueous media with chelating activity for an essential metal. The method comprises providing a first monomer unit comprising one or more suitable metal binding chemical groups incorporated or affixed thereto and polymerizing the first monomer unit with at least a second monomer unit by a reversible addition fragmentation chain transfer mechanism with the use of a suitable addition fragmentation chain transfer agent. The resulting chelating composition binds one or more essential metals in the environment of a living cell or organism and thereby affects the living cell or organism.

RAFT polymerization is regarded as a living type of polymerization where a higher degree of control over the polymerization can be achieved compared to free radical polymerization (FRP). In the context of the present invention, the use of RAFT polymerization can improve quality and yields of the resulting product compared with FRP. RAFT polymerization allows for more efficient utilization and incorporation of the first monomer unit, which is typically the more difficult to prepare and therefore more costly, into the polymer. The ability to efficiently incorporate the first monomer unit into the resulting polymer greatly improves the overall yield of the polymerization reaction. Additionally, RAFT polymerization allows for control of the molecular weight during the polymerization resulting in a polydispersity index (PDI) approaching unity characterized by a narrow distribution range of molecular weights of the resulting polymerized compounds.

RAFT polymerization employs a suitable addition-fragmentation chain transfer agent, also known as a RAFT agent, which participates in the polymerization reaction itself and is effective for controlling the rate of radical transfer to mediate a more uniform polymerization. There are a wide variety of addition-fragmentation chain transfer agents known in the art and these are generally commercially available and often employed for polymerization in non-aqueous solvent systems. In one embodiment, the addition-fragmentation chain transfer agent is soluble and active in aqueous media, i.e., capable of participating in radical transfer for polymerization in aqueous systems for the purposes of obtaining aqueous prepared metal chelating co-polymers. In another embodiment, the addition-fragmentation chain transfer agent is soluble in organic media. In this embodiment, the polymerization can be performed in an organic solvent and the polymerized product can be further treated to be soluble in aqueous media. It should be noted however, that polymerization of the chelating compositions of the present invention can also be performed in non-aqueous media such as in organic solvents provided that the resulting chelating composition product is substantially soluble in aqueous media for use. Generally, addition-fragmentation chain transfer agents fall into three classes: dithiobenzoates, trithiocarbonates and dithiocarbamates, represented generally by the structures below.

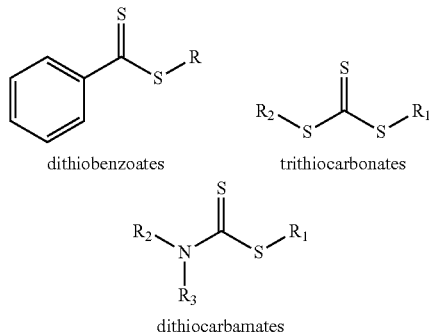

The present invention contemplates the use of any suitable addition-fragmentation chain transfer agent in these classes and any other class of agents.

RAFT chemical processes are well known in the art and have been used to prepare various polymer materials including homo-polymer materials, which can then be chemically modified (i.e., post polymerization modification) to add metal binding pyridinone containing chemical groups through chemical conjugation (Junpei Li, et al. *Polymer*, 2016, 87, 64-72, herein incorporated by reference). However, RAFT processes have not been applied to co-polymer compositions prepared with a metal chelating monomer unit when directly co-polymerized with one or more non-chelating monomers.

In an embodiment of the chelating composition and method of its preparation, the one or more suitable metal binding chemical groups are independently selected from the group consisting of the carboxyl, hydroxyl, phenolate, catecholate, hydroxamate, hydroxypyridinone and hydroxyphenyltriazole chemical types.

In a particular embodiment, the one or more suitable metal binding chemical groups are the hydroxypyridinone chemical type

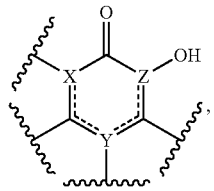

wherein X, Y and Z is independently N or C such that:
when X is N, Y and Z are C,
when Y is N, X and Z are C, and
when Z is N, X and Y are C.

In a further embodiment of the chelating composition and the method of preparation thereof, the first monomer unit is represented by Compound (I)

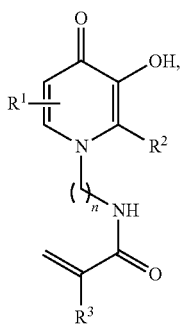

Compound (I)

wherein
$R^1$ is independently selected from the group consisting of H, alkyl and alkyl substituted with O, N or S;
$R^2$ is independently selected from the group consisting of H, alkyl and alkyl substituted with O, N or S;
$R^3$ is independently selected from the group consisting of H, alkyl and alkyl substituted with O, N or S; and
n is 1 to 12.

Compound (I) may be prepared by polymerizing Compound (Ia)

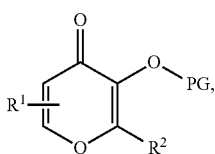

Compound (Ia)

wherein
$R^1$ is independently selected from the group consisting of H, alkyl and alkyl substituted with O, N or S;
$R^2$ is independently selected from the group consisting of H, alkyl and alkyl substituted with O, N or S; and
PG is a protecting group,
with Compound (Ib)

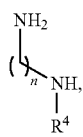

Compound (Ib)

wherein
n is 1 to 12; and
$R^4$ is $COCCH_2R^3$ or a protecting group,
by a reversible addition-fragmentation chain transfer mechanism with the use of a suitable addition-fragmentation chain transfer agent.

The preparation of Compound (I) is completed by:
when $R^4$ is $COCCH_2R^3$, removing PG; or
when $R^4$ is a protecting group, removing $R^4$, reacting with a suitable acrylate source, and removing PG.

In the preparation of Compound (Ib) when $R^4$ is $COCCH_2R^3$, Compound (Ib) may be prepared by reacting a suitable acrylate source with an alkanediyl diamine.

It is understood that the use of any suitable hydroxy and amine protecting group is contemplated in the present invention. Examples of suitable protecting groups are presented in Greene (Wuts, Peter G. M., and Greene, Theodora W., *Greene's protective groups in organic synthesis*. John Wiley & Sons, 2006) and Jarowicki (Jarowicki, Krzysztof and Kocienski, Philip. *Contemp. Org. Synth.* 1997, 4, 454-492 herein incorporated by reference). For example, a suitable hydroxy protecting group may be a benzyl ether, alkyl ether, substituted alkyl ether, allyl ether, silyl ether, acetate, benzoate, or alkoxyalkyl ether protecting group and a suitable amine protecting group may be an alkyl carbamate, substituted alkyl carbamate, benzyl carbamate, acetamide, substituted acetamide, phthalimide, benzylamine, benzylideneamine, or substituted sulfonamide protecting group.

In one embodiment, PG of Compound (Ia) is a benzyl ether protecting group.

In a further embodiment, when $R^4$ is a protecting group in Compound (Ib), the protecting group is a tert-butyloxycarbonyl protecting group.

Further, the benzyl ether protecting group and the tert-butyloxycarbonyl protecting group may be removed by treatment with acid. However, any other suitable means for removing the protecting group is contemplated and will be known by one skilled in the art.

In one embodiment of the chelating composition, the composition is prepared from Compound (I) wherein:
$R^1$ is H;
$R^2$ is methyl;
$R^3$ is methyl; and
n is 1 to 6.

In a further embodiment of the chelating composition, the composition is prepared from Compound (I) wherein:
$R^1$ is H;
$R^2$ is methyl;
$R^3$ is methyl; and
n is 2.

The chemical name for the above compound is 3-hydroxy-1-(β-methacrylamidoethyl)-2-methyl-4(1H)-pyridinone, abbreviated as MAHMP, and is represented by Compound (II) below.

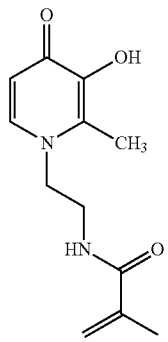

Compound (II)

US patent application publication No. US2016/0038604 A1, incorporated herein by reference, discloses the synthesis of Compound (II). The synthesis of Compound (II) is presented in FIG. 1. According to this synthesis, MAHMP is prepared through a sequence of chemical steps starting with 3-hydroxy-2-methyl-4-pyrone (structure 1) through to the preparation of 1-aminoethyl-3-hydroxy-2-methyl-4(1H)-pyridinone (AHMP, structure 4) with the latter being treated with methacryloyl chloride to ultimately yield Compound (II).

Using a synthesis procedure of the present invention, Compound (II) can be produced in higher yields as compared to the previous method. This is, in part, as a result of the present synthesis not having a requirement for the preparation of an intermediate product and requiring an overall reduced number of synthesis steps.

The present invention also provides for a chelating composition and method of preparation thereof in which the second monomer unit is independently selected from the group consisting of 1-vinyl-2-pyrrolidone, acrylic acid, methyl methacrylate, N,N-dimethyl-acrylamide, ethyl methacrylate, N-vinyl imidazole and styrene.

In one example of the chelating composition and method of preparation thereof, the first monomer unit is Compound (II) and the second monomer unit is 1-vinyl-2-pyrrolidone.

In another example of the chelating composition and method of preparation thereof, the first monomer unit is Compound (II) and the second monomer unit is N,N-dimethyl-acrylamide.

Figure 9:
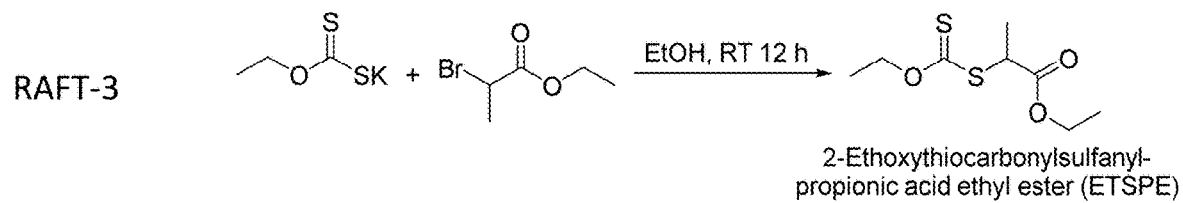
FIG. 9 shows the synthesis schemes for RAFT agents RAFT-3, RAFT-4 and RAFT-5 as described in Example 9.
Figure 9:
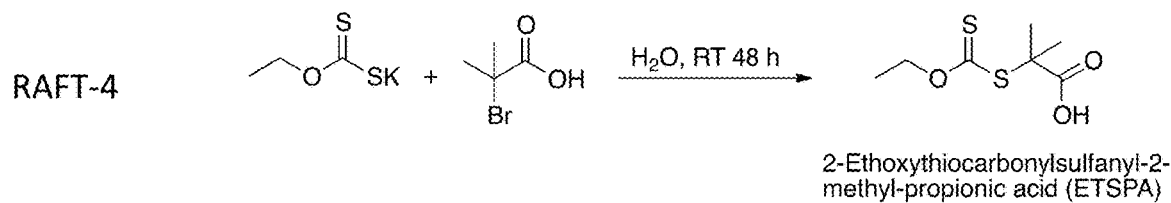
Figure 9:
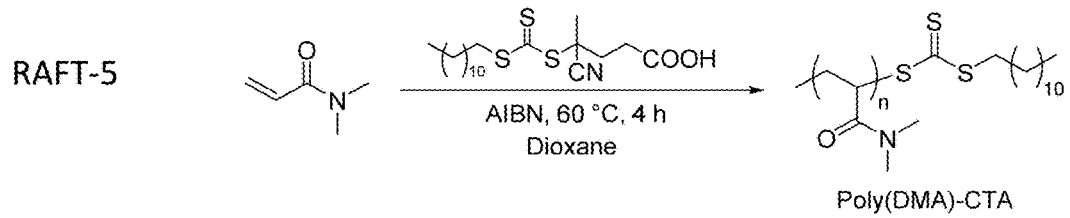

In further embodiments, without wishing to be limiting, the addition-fragmentation chain transfer agents are independently selected from the group consisting of 2-ethoxy-thiocarbonyl sulfanyl-2-methyl-propionic acid (ETSPA), 2-ethoxythiocarbonylsulfanyl-propionic acid ethyl ester (ETSPE) and poly(N,N-dimethylacrylamide) 4-cyano-4-[(dodecylsulfonylthiocarbonyl)sulfanyl]pentanoic acid (poly-DMA CTA), presented in FIG. 9. In a further embodiment, the addition-fragmentation chain transfer agent is ETSPA and ETSPE, and in particular ETSPA. It is noteworthy that the invention is not limited to the above addition-fragmentation chain transfer agents and other addition-fragmentation chain transfer agents may perform favorably.

Furthermore, it is contemplated that the addition-fragmentation chain transfer agent is removed in whole or in part from the chelating composition after polymerization. This can be achieved by any means known in the art, for example filtering off the addition-fragmentation chain transfer agent or precipitating the chelating composition from the solution in which the addition-fragmentation chain transfer agent is solubilized.

The chelating compositions described herein may have one or more different structural architectures depending on how the individual monomers are arranged in the co-polymer. These types of structural architectures generally include:
- alternating, wherein the first and second monomers alternate regularly, with nearly equivalent amounts in each chain, for example A-B-A-B-A-B-A-B;
- periodic, wherein a section of the monomers are repeated within the chain, for example A-B-B-A-B-B-A-B-B;
- diblock, comprising one block composed of one monomer grafted to a second block composed of a different monomer, for example A-A-A-A-B-B-B-B;
- triblock, comprising three blocks, each block composed of the same monomer, grafted together, for example A-A-A-A-B-B-B-B-A-A-A-A or A-A-A-A-B-B-B-B-C-C-C-C; or
- multiblock, comprising different combination and numbers of blocks.

In addition, the chelating compositions may have one or more different morphologies. These morphological forms include linear, branched, brush, comb or star.

A further embodiment of the chelating composition and method of preparation includes the removal of the 3-hydroxy protecting group, PG, after the polymerization step. Thus, in an embodiment of the chelating composition and method of preparation, the first monomer unit is represented by Compound (III)

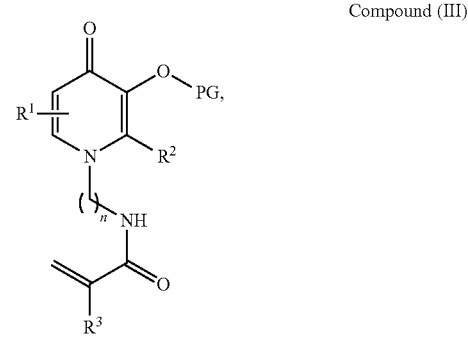

Compound (III)

wherein
R[1] is independently selected from the group consisting of H, alkyl and alkyl substituted with O, N or S;
R[2] is independently selected from the group consisting of H, alkyl and alkyl substituted with O, N or S;
R[3] is independently selected from the group consisting of H, alkyl and alkyl substituted with O, N or S;
n is 1 to 12; and
PG is a protecting group.

Following polymerization with the second monomers by a RAFT mechanism with the use of a suitable addition-fragmentation chain transfer agent, the 3-hydroxy protecting group is removed by suitable means.

The chelating compositions described herein may have a molecular size which is generally sufficiently large so as not to be readily taken up into a bacterial, fungal, parasitic or cancer cell or readily recognized and bound by cell surface receptors that could facilitate iron removal from the composition to deliver iron to the internal aspects of the cell. On the other hand, there is no limit to the upper molecular weight limit, provided only that the upper molecular weight is sufficiently low so as to still permit the chelating composition to remain soluble at least before it binds with metal in aqueous media and environments of intended use. In one embodiment of the present invention, the chelating composition has a lower molecular weight limit of around 1500 Daltons and has no upper molecular weight limit provided it remains soluble in aqueous media prior to the binding of metal. For example, the chelating composition may be at least 1500, 5000, 10 000, 50 000, 100 000, 200 000, 300 000, 400 000, 500 000, 1 000 000, 1 500 000, 2 000 000, 2 500 000, or 3 000 000 Daltons. Further, the molecular weight may comprise a range defined by any two values listed above or any two amounts therein between. In one embodiment, the soluble chelating composition, even when provided as a low molecular weight composition, would not be readily recognized by the cell or the cell's receptor and uptake mechanisms.

It is to be understood that in various embodiments, the essential metal is iron, manganese, copper, cobalt, magnesium or nickel. In a particular embodiment, the essential metal is iron.

In relation to the chelating compositions of the present invention, the living cell or organism is affected in its growth or activities by having insufficient amounts of the essential metal available for its use.

In one embodiment, the metal chelating composition may be used for the treatment of a disease in an animal, including a fish or a human, that has a disease attributable to a cell or cells, or the activity of the cell or cells, wherein the cell or cells causing the disease are one or more of a microbial cell, a cancer cell or, a uni-cellular or multi-cellular parasitic organism.

In one embodiment, the metal chelating composition may be used in the manufacture of a medicament for the treatment of a disease in an animal, including a fish or a human, that has a disease attributable to a cell or cells, or the activity of the cell or cells, wherein the cell or cells causing the disease are one or more of a microbial cell, a cancer cell or, a uni-cellular or multi-cellular parasitic organism.

In a further embodiment, there is also provided a method of treating a disease in an animal, including a fish or a human, by administrating a therapeutically effective amount of the chelating composition described herein, wherein the disease is caused by a cell or cells, or the activity of the cell or cells, wherein the cell or cells causing the disease are one or more of a microbial cell, a cancer cell or a uni-cellular or multi-cellular parasitic organism.

In a further embodiment, the metal chelating composition is for administration to an animal, including a human or a fish. The chelating compositions may be administered into the body, for example by injection, or be applied onto the body, for example onto epithelial surfaces. The chelating compositions may also be combined with wound dressing materials, for example hydrogels, coatings, sutures, bandages, and other dressing materials, to help control microbial growth at wound sites or with materials utilized to manufacture indwelling medical devices, such as catheters, shunts and other indwelling medical devices, so as to interfere with microbial growth on such devices. Owing to the solubility of the chelating compositions in aqueous media, these can diffuse into wound sites or from medical devices to bind metal and restrict its availability to pathogenic cells.

In an even further embodiment, the metal chelating composition is for administration to an animal, including a human or a fish, in conjunction with another anti-cellular agent comprising one or more of an anti-microbial agent, an anti-metabolite agent, an anti-viral agent, an anti-parasitic agent or an anti-cancer agent. The anti-cellular agents referred to are agents that generally permeate into the target cell and then injure and ultimately kill the target cell, be it a pathogenic fungal, bacterial, parasite or cancer cell. Utilizing a chelating composition of the present invention with the anti-cellular agent may provide an alternative ability of controlling the growth or activity of the cell treated or an enhanced cell killing effect from the anti-cellular agent.

Without being limiting, the anti-microbial, anti-metabolite, anti-viral, anti-parasitic or anti-cancer anti-cellular agents may be independently selected from, for example: penicillins, cephems, cephalosporins, carbapenems, penems, monocyclic 1-lactams, macrolides, ketolides, streptogramins, lincosamines, fluoroquinolones, coumarin antibiotics, glycopeptides, monobactams, lipoglycopeptides, ansamycins, phenicols, nitroimidazoles, fosfomycin, orthosomycins, paldimycin, primycin, benzonaphthyridones, mutilins, oxazolidinones, sulfonamides, nitrofurans, polyenes, benzylpyrimidines, bacitracin, chloramphenicol, tetracyclines, erythromycins, clindamycin, gentamicin, aminoglycosides, mupirocin, fusidic acid, spectinomycin, rifamycins, quinolones, ciprofloxacin, nitrofurantoin, 5-fluorocytosine, trimethoprim, sulfonamides, trimetrexate, imidazoles, triazoles, zidovudine, ganciclovir, vidirabine, acyclovir, amantidines, idoxuridine, foscarnet, trifluridine, ribavirin, penciclovir, stavudine, quinolines, quinoline derivatives, diaminopyrimidines, halofantrine, pyrimethamine, chloroguanide, quinine, atovaquone, diloxanide furoate, eflornithine, melarsoprol, metrondiazole, nitrofurans, pentamidine, other diamidines, sodium stibogluconate, suramin, nitrosourea, fluorouracil bleomycin, anti-microbial peptides, antimicrobial surfactants, halogens, aldehydes, other antimicrobial organic chemicals or chemically related compounds of any of the foregoing and/or derivatives of any of the foregoing.

In a further embodiment, the chelating composition may be administered with an anti-microbial preservative agent. Utilizing a chelating composition of the present invention with the preservative agent may provide an alternative ability of controlling the growth or activity of the cell treated or an enhanced preservative effect from the preservative agent. Without being limiting, the anti-microbial preservative is independently selected from: propionic acid and propionates; sorbic acid and sorbates; benzoic acid and benzoates; sodium diacetate; lactic acid; sulfur dioxide, sulfites; sodium nitrite; sodium chloride; aldehyde containing or releasing compounds, mercury containing compounds; antioxidants; detergents such as quaternary ammonium compounds and complexing agents such as ethylene-diamine-tetra-acetic acid.

Combining the chelating compositions with anti-cellular agents and anti-microbial agents can be especially useful for cells or parasitic organisms that possess a degree of resistance to the chemical anti-cellular agent. The purpose of exploiting the chelating composition as above is one or more of: compromising the ability of the cells or parasitic organisms to grow; increasing the undesirable cell's or parasitic organism's sensitivity to the chemical anti-cellular agent being used, or to help overcome the degree of resistance possessed by the undesirable cell or parasitic organism to the chemical anti-cellular agent or anti-microbial preservative agent being used for treatment.

The present invention also provides for a pharmaceutical composition comprising the chelating composition described herein and a pharmaceutically acceptable carrier.

The present invention also provides for a pharmaceutical composition comprising the chelating composition described herein and an anti-cellular agent and/or a microbial preservative agent.

The chelator compositions of the present invention may be added or incorporated into an aqueous medium to be treated in any suitable, effective amount so as to provide the desired or necessary control of cell growth or affect a cell activity. The amount of chelator composition of the present invention to associate with an aqueous medium will depend, for example, on the type of aqueous system to be treated (in vitro or in vivo), on the contained amount of iron and/or other essential metal to be bound up by the chelator composition, on the type of cell to be targeted, for example bacteria, yeast, parasite or cancer cell, and on the desired outcome, for example to prevent growth or to affect a particular cell activity.

It should be appreciated that administration of the soluble chelation compositions described herein to an animal including a human or a fish would require the administration of a sufficient dosage so as to achieve effective concentrations at the site in the host where the soluble chelating composition is to function, for example in the blood or vaginal fluid. Generally, the chelation composition would be added or administered so as to achieve an excess, for example, a two to five-fold excess, of iron and/or other essential metal chelating capacity over the amount of iron and/or other metal concentration present in the aqueous environment at the site to be treated when control of growth is the desired outcome and when used without an anti-cellular agent. It should be appreciated that smaller effective dosages would be expected if the soluble chelating composition is administered in conjunction with an anti-cellular agent for the purpose of lowering the resistance of the cell to the anti-cellular agent.

It is to be understood herein that the various chelating compositions described above are to be chosen keeping in mind the environment of intended use thereof; i.e. the chelating compositions are to be selected such that the compositions work in an acceptable fashion in the environment of intended use. For example, in the context of pharmaceutical or food applications, the chelating compositions are to be chosen so as to provide a pharmaceutically acceptable substance, for example a pharmaceutically safe preparation, or the like. The chelating compositions as described herein may, for example, have applications in relation to cosmetics, for example as a preservative type material, and would thus have to be acceptable in the context of this type of application of the invention.

It will be appreciated that the reference herein to "essential metals" is a reference to the metal(s) needed by a cell for growth and/or maintenance.

It is further to be appreciated that if a "member of a series", "group of substances", "group of substituents", "range" of a particular characteristic (e.g. molecular weight, temperature, concentration, time and the like) or the like is mentioned, the present invention relates to and explicitly incorporates herein each and every specific member and combination of sub-ranges or sub-groups therein. Thus, any specified series, range or group is to be understood as a shorthand way of referring to each and every member of a series, range or group individually as well as each and every possible sub-series, sub-ranges or sub-groups encompassed therein. Thus, for example,

- with respect to the number of carbon atoms, the mention of the range of 1 to 12 carbon atoms is to be understood herein as incorporating each and every individual number of carbon atoms as well as sub-ranges such as, for example, 2 carbon atoms, 4 to 6 carbon atoms, etc.;
- with respect to a molecular weight (e.g. avg. molecular weight) greater than 1500 Daltons, it is to be understood herein that (subject to the solubility requirement mentioned herein) the molecular weight may be far ranging e.g. a molecular weight greater than 5000 Daltons, a molecular weight greater than 1500 Daltons, a molecular weight of 1500 to 10 000 000 Daltons, a molecular weight of 15 000 to 10 000 000 Daltons, a molecular weight of 1500 to 3 000 000 Daltons, a molecular weight of 1500 to 2 000 000 Daltons, a molecular weight of 10 000 Daltons, a molecular weight of 80 000 Daltons, a molecular weight of 100 000 Daltons, etc.
- with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

and similarly with respect to other parameters such as concentrations, elements, etc.

It is to be understood herein that reference to alkyl includes a straight chain alkyl group, for example and without limitation, methyl, ethyl, propyl, butyl, pentyl, hexyl, heptyl, octyl, nonyl, decyl, undecyl and dodecyl. In one embodiment, alkyl refers to $C_{1-12}$ alkyl or a subset thereof, for example a $C_{1-6}$ alkyl and a $C_{1-3}$ alkyl. Also included is a branched alkyl group, for example and without limitation, iso-butyl, tert-butyl, 2-pentyl (i.e. 2-methyl-butyl), 3-pentyl (i.e. 3-methyl-butyl, isopentyl), neopentyl and tert-pentyl. The alkyl group may also be independently saturated, unsaturated or substituted. Substitutions of the alkyl include heteroatom substitutions, for example and without limitation, O, N and S.

It is to be understood herein that classes or sub-classes are inherently defined herein in every and any possible manner whatsoever. The classes or sub-classes or individual components of the classes or sub-classes include both positive as well as negative or exclusionary definitions i.e. the definitions herein incorporate any and all definitions that may be worded as positively including particular individual compounds, classes or sub-classes and/or as excluding particular individual compounds, classes or sub-classes or combinations thereof; for example an exclusionary definition for the definition of a compound formula may read as follows: "provided that when one of $R_1$ and $R_2$ is methyl and the other is H, $R_8$ may not occupy the 2 position".

It is also to be understood that in the context of the present invention, suitable RAFT agents include any of those as previously described or as to be designed, as for example described by Keddie (Keddie, D. J, et al. *Macromolecules*, 2012, 45, 5321-5342, herein incorporated by reference), provided that they are useful for obtaining a suitable RAFT mediated polymer composition.

Various embodiment of chelating compositions have been described. The above-described embodiments are intended to be examples and alterations and modifications may be effected thereto by those of ordinary skill in the art without departing from the spirit and scope of the teaching.

EXAMPLES

The following non-restrictive examples are provided to illustrate various aspects of the present invention while not in any way being intended to limit the scope of the invention.

Example 1; Conventional Synthesis of 3-hydroxy-1-(β-methacrylamidoethyl)-2-methyl-4(1H)-pyridinone (MAHMP) Chelating Monomer Useful for Preparation of Chelating Compositions Through Preparation of the Intermediate 1-aminoethyl-3-hydroxy-2-methyl-4(1H)-pyridinone (AHMP)

The synthesis of this chelating monomer intermediate has been previously described elsewhere (U.S. patent application Ser. No. 14/124,619, PCT/CA2012/000562). This example is provided to show the relatively complex nature of the previously disclosed synthesis procedures with its various time-consuming steps and the problematic low product yield that is obtained. FIG. 1 shows the overall sequence of steps and reference is made to the chemical intermediates (structure 1) through (structure 5) in the example below.

A. Preparation of a Protected Pyridinone Precursor

To a 20 L flask were added: 7.93 mol 3-hydroxy-2-methyl-4-pyrone (structure 1, FIG. 1), 10.2 L methanol, 11.9 mol benzyl chloride and a solution of 8.33 mol sodium hydroxide in 1.12 L water to give a pale yellow clear solution. The mixture was refluxed for six hours and then stirred at room temperature overnight. Methanol was evaporated using vacuum and the residue (yellow orange oil) was mixed with 4.5 L water and extracted using three separate 2.5 L aliquots of methylene chloride. The three methylene chloride extracts were pooled and washed with three changes of 1.2 L 5% NaOH and then three changes of 1.2 L water. The methylene chloride extract was then dried over solid $MgSO_4$. Following filtration to remove the $MgSO_4$ and evaporation of the solvent, 1.8 kg of crude 3-benzyloxy-2-methyl-4-pyrone (structure 2, FIG. 1) was recovered representing a crude yield of 105%. $^1H$ NMR in $CDCl_3$ (400 MHz) δ 7.58 (d, 1H), 7.40-7.29 (m, 5H), 6.35 (d, 1H), 5.13 (s, 2H), 2.06 (s, 1H).

Structure 2 represents an example of a protected pyridinone compound as a preferred intermediate for the subsequent synthesis steps to methacrylamidoethyl-2-methyl-4 (1H)-pyridinone (MAHMP) or its related 3-hydroxy-1-(β-methacrylamido-R)-2-methyl-4(1H)-pyridinone series of compounds where R is a hydrocarbon chain of length ≥1 and ≤12 carbon units. It should be noted that alternate methods providing different pyridinone starting materials, alternate protecting groups and alternate methods for preparing protected pyridinone precursors are possible and such methods would be suitable provided these provide both suitable protection of the pyridinone group and also permit the subsequent preparation of 3-hydroxy-1-(β-methacrylamido-ethyl)-2-methyl-4(1H)-pyridinone (MAHMP) or its related 3-hydroxy-1-(β-methacrylamido-R)-2-methyl-4(1H)-pyridinone series of compounds are synthesized where R is a hydrocarbon chain of length ≥1 and ≤12 carbon units.

B. Preparation of Intermediate 1-aminoethyl-3-hydroxy-2-methyl-4(1H)-pyridinone (AHMP)

From the crude 3-benzyloxy-2-methyl-4-pyrone material prepared in A., 6.01 mol was mixed in a 20 L flask with 8.5 L ethanol, 27.95 mol ethylenediamine and 34 mL water and stirred overnight at room temperature. The solvent and excess ethylenediamine were removed under reduced pressure to yield a yellow-brown oily liquid that was triturated with 7 L water and the aqueous layer was then extracted using three separate 3 L aliquots of methylene chloride (Note: Triturating with water prior to extraction with methylene chloride gave a solid during small scale synthesis). When this protocol was followed on a larger scale, the material did not solidify and was thus extracted with methylene chloride and concentrated. The three methylene chloride extracts were combined and concentrated under reduced pressure to yield 1.17 kg (76%) of 1-(2-aminoethyl)-3-benzyloxy-2-methyl-4-(1H)-pyridinone (structure 3, FIG. 1) as a yellow brown oil-like material. $^1H$ NMR in $d_6$-DMSO (400 MHz) δ 7.54 (d, 1H), 7.38-7.30 (m, 5H), 6.11 (d, 1H), 4.99 (s, 2H), 3.8 (t, 2H), 3.70 (t, 2H), 2.15 (s, 3H). To a 20 L flask were charged 4.57 mol of 1-(2-aminoethyl)-3-benzyloxy-2-methyl-4-(1H)-pyridinone (structure 3, FIG. 1), 8.96 L 6 M aqueous HCl and the solution was stirred at room temperature overnight. A pale yellow solid was recovered after evaporation to dryness in vacuum. This was re-dissolved in 8.96 L 6 M aqueous HCl and stirred at room temperature for four days and evaporated to dryness again. The solid residue was washed with acetone (enough to make the solid free and filterable) and filtered to obtain the crude yellow solid. To this crude material were added 4 M aqueous HCl (2 L) and ethanol (1 L) and the mixture was refluxed until the solids had dissolved. The product was then re-crystallized by storage in a refrigerator, filtered, washed with acetone and dried under reduced pressure to yield AHMP (130 g, 14% yield). The final 1-aminoethyl-3-hydroxy-2-methyl-4(1H)-pyridinone (AHMP) product (structure 4, FIG. 1) was yellow. $^1H$ NMR in $d_6$-DMSO (400 MHz) δ 10.41 (bs, 1H), 8.56 (s, 3H), 8.33 (d, 1H), 7.35 (d, 1H), 4.66 (t, 2H), 3.27 (t, 2H), 2.55 (s, 3H).

C. Preparation of 3-hydroxy-1-(β-methacrylamido-ethyl)-2-methyl-4(1H)-pyridinone (MAHMP) Monomer To a 2 L flask fitted with a magnetic stirrer and a dropping funnel, 0.488 mol of AHMP prepared as in B above (structure 4, FIG. 1) was dissolved in 413 mL water. Thereafter, 1.46 mol triethylamine ($Et_3N$) and 826 mL $CH_3CN$ (acetonitrile) were added and the mixture was placed on an ice bath. Methacryloyl chloride ($C_3H_3ClO$), 0.488 mol, was then added drop-wise over 1.5 h while the mixture was kept in the ice bath (0-5° C.). Following this addition, mixture was allowed to warm to room temperature and stirring was continued for two hours. The mixture was then evaporated to dryness and 2 L hot acetone was added to the solid residue and filtered. In addition to solids filtered some crystals of triethylammonium chloride were observed in the filtrate which were removed by second filtration and the filtrate was evaporated to remove approximately 800 mL of the acetone and then it was stored in a refrigerator overnight. An initial needle crystal of triethylammonium chloride, if formed, was removed by filtration and the filtrate was returned to the refrigerator for 18 h and filtered to yield a light yellow solid (76 g). The solid obtained was stirred with 190 mL acetone for 4 h and filtered to yield 50 g (43.4% yield) of 3-hydroxy-1-(β-methacrylamidoethyl)-2-methyl-4(1H)-pyridinone (MAHMP) (structure 5, FIG. 1) as off white solid [Note: After the entire process above was carried out, NMR analyses sometimes showed the presence of triethylammonium chloride as an impurity in some batches. This was removed by slurrying in chloroform (2.5 volume, 3 h) followed by filtration]. $^1H$ NMR in $d_6$-DMSO (400 MHz) δ 8.08 (bs, 1H, NH), 7.37 (d, 1H, ArH), 6.06 (d, 1H, ArH), 5.59 (s, 1H, =CHaHb), 5.33 (s, 1H, =CHaHb), 4.86 (bs, 1H, —OH), 4.02 (t, 2H, —$NCH_2$), 3.37 (t, 2H, —$NCH_2$), 2.28 (s, 3H, —$CH_3$), 1.81 (s, 3H, —$CH_3$) confirmed the product 3-hydroxy-1-(β-methacrylamidoethyl)-2-methyl-4(1H)-pyridinone (MAHMP) (structure 5, FIG. 1) but the overall yield of the synthesis route was only 8.9% (wt/wt).

This example (A-C above) shows the relatively complex conventional synthesis route with various steps and the undesirable problematic low yield of the final MAHMP product, i.e., less than 10% overall yield.

Example 2A; Novel Synthesis of 3-hydroxy-1-(β-methacrylamidoethyl)-2-methyl-4(1H)-pyridinone (MAHMP) Chelating Monomer Useful for Preparation of Chelating Compositions without Preparation of Intermediate 1-aminoethyl-3-hydroxy-2-methyl-4 (1H)-pyridinone (AHMP)

Figure 2A:
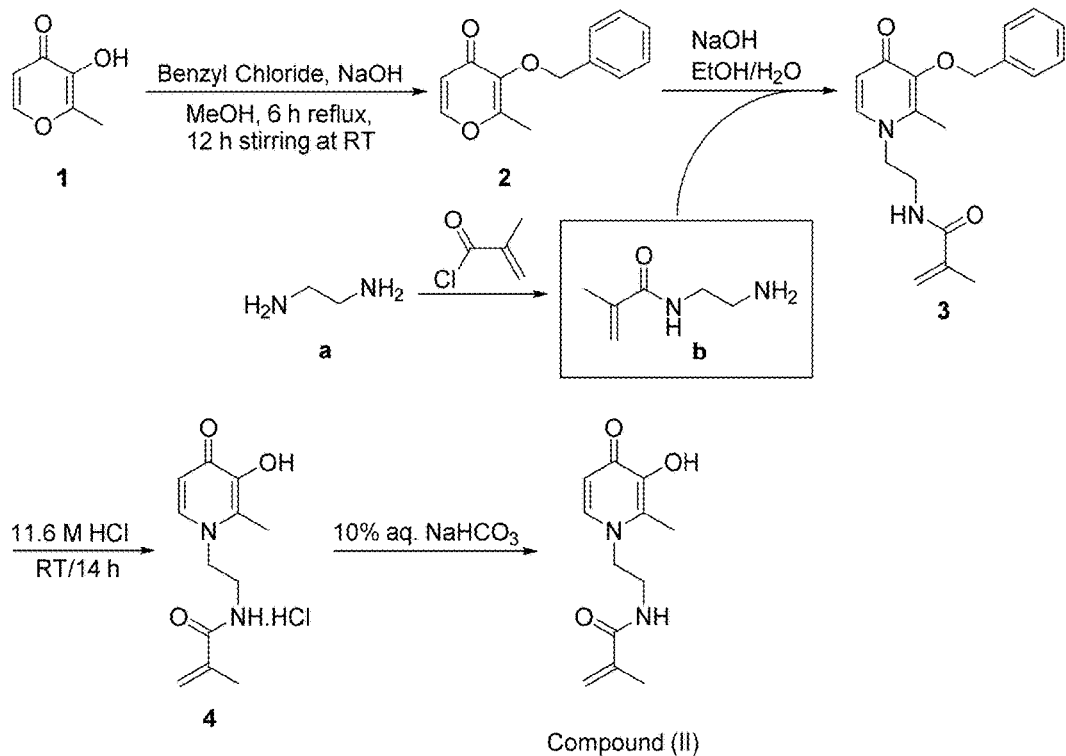
FIG. 2A shows the overall chemical synthesis sequence for the novel synthesis of 3-hydroxy-1-(β-methacrylamidoethyl)-2-methyl-4(1H)-pyridinone (MAHMP, Compound (II)) chelating monomer useful for preparation of chelating compositions without need for preparation of conventional key intermediate 1-aminoethyl-3-hydroxy-2-methyl-4(1H)-pyridinone (AHMP) as detailed in Example 2.

FIG. 2A shows the overall sequence of steps and reference is made to the chemical intermediates (structure 1 through to Compound II and structure a and structure b) in the example below.

3-hydroxy-2-methyl-4-one (structure 1, FIG. 2A) was used to prepare 3-(benzyloxy)-2-methyl-4H-pyran-4-one (structure 2, FIG. 2A) as described for Example 1A.

Synthesis of N-(2-aminoethyl)methacrylamide (structure b, FIG. 2A) was completed as follows: In a 20 L round bottom flask were charged ethylenediamine (320 mL; 0.91 eq; 4.35 mol) (structure a, FIG. 2A) and water (4.8 L). Then pH was adjusted to 8.5 with 3 N HCl at 0° C. To this stirred solution, a solution of methacrylolyl chloride (500 g; 1.0 eq; 4.78 mol) in chloroform (3.2 L) was added dropwise over 3 h at 0° C. The mixture was stirred at RT overnight. From the biphasic reaction mixture the organic and aqueous phase were then separated and the aqueous layer was washed with chloroform (1 L). The aqueous layer was then concentrated under vacuum to yield a white solid that was subjected to stirring in methanol (4 L) followed by filtration to remove a white solid. The filtrate was then concentrated to yield a white semisolid which was stirred in 2M NaOH solution (3 vol) and extracted with 10% isopropyl alcohol (IPA) in CHCl$_3$ (5×1500 mL). The 5 organic fractions were combined and dried over sodium sulfate and concentrated under reduced pressure to yield a pale yellow semisolid (145 g) representing a product yield of 23.6%. $^1$H NMR confirmed the identity of N-(2-aminoethyl)methacrylamide (structure b, FIG. 2A) and HPLC confirmed a purity of 99.3% and 98.6 by LCMS. $^1$H NMR (400 MHz, d$_6$-DMSO) δ 7.82 (bs, 1H), 5.69 (s, 1H), 5.29 (s, 1H), 3.09 (t, 2H), 2.57 (t, 2H), 1.84 (s, 3H). 1.38 (bs, 2H).

Example 2B: Alternative Syntheses of N-(2-aminoethyl)methacrylamide Using N-Hydroxysuccinimide Methacrylate (Path A) and Methacrylic Anhydride as the Methacrylate Source (Path B)

Figure 2B:
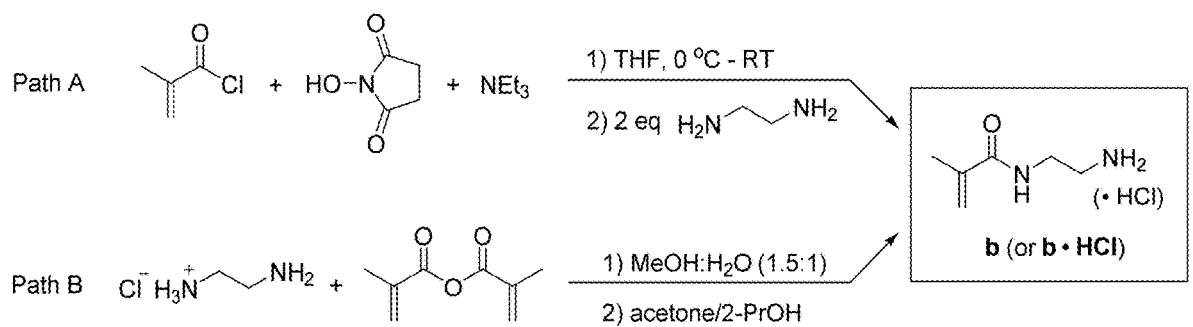
FIG. 2B shows two alternative synthesis schemes (Path A and B) for structure b of FIG. 2A.

An alternate procedure for the synthesis of N-(2-aminoethyl)methacrylamide (structure b, FIG. 2B, Path A) was completed by first synthesizing N-hydroxysuccinimide methacrylate. N-hydroxysuccinimide (11 g, 95.7 mmol) was added to a 3-neck flask under a nitrogen atmosphere whereupon 300 mL of anhydrous tetrahydrofuran (THF) was added. To this triethylamine (13.3 mL, 95.7 mmol) was added to the solution and left to stir for 1 h at room temperature. The solution was then cooled to 0° C. and methacryloyl chloride (9.3 mL, 95.7 mmol) was added dropwise to the solution. The solution was then allowed to warm up to room temperature and left to stir overnight. The precipitate was filtered off and the solvent was removed under reduced pressure. The residue crystallized from methanol was N-hydroxysuccinimide methacrylate (75% yield). $^1$H NMR (400 MHz, d$_6$-DMSO): δ 6.35 (s, 1H), 6.10 (s, 1H), 2.84 (s, 4H), 2.00 (s, 3H). N-hydroxysuccinimide methacrylate (5 g, 27 mmol) was added to a 3-neck flask under a nitrogen atmosphere. To this 400 mL of anhydrous THF was added with stirring. The resultant mixture was cooled to 0° C. To the cooled mixture, ethylenediamine (3.6 mL, 54 mmol) was added, whereupon a white precipitate immediately formed. The reaction mixture was allowed to warm to room temperature and stirred overnight. The following day, the white precipitate was filtered off by gravity filtration and washed with THF (3×100 mL). The filtrate and THF washings were collected and the solvent was removed under reduced pressure to yield and off-white semi-solid and this was found to be mixture of structure b and di-substituted ethylenediamine with methacrylate. $^1$H NMR confirmed a 90% monoamine (structure b) from the starting ester. $^1$H NMR (400 MHz, d$_6$-DMSO): δ 7.84 (bs, 1H), 5.64 (s, 1H), 5.31 (m, 1H), 3.11 (q, 2H), 2.49 (t, 2H), 1.85 (s, 3H), 1.36 (bs, 2H).

The hydrochloride salt of N-(2-aminoethyl)methacrylamide (structure b.HCl, FIG. 2B, Path B) can be synthesized and used directly in the synthesis of structure 3. Ethylenediamine (11.1 mL, 0.2 mol, 2.0 equiv) was added to a solution of ethylenediamine dihydrochloride (11 g, 0.08 mol, 1.0 equiv) in 100 mL of water. After 1.5 h of stirring at room temperature, methanol (110 mL) was added and the mixture was cooled to 0° C. allowing a temperature equilibration of 15 min. Methacrylic anhydride (37 mL, 0.25 mol, 3.0 equiv) dissolved in methanol (40 mL) was added dropwise over 30 min to the cooled solution. After complete addition of the methacrylic anhydride, the solution temperature was maintained at 0° C. for 1 h. Hydrochloric acid (20 mL) was added to the solution and stirring continued for 1 h allowing the solution to warm up to room temperature. The solvent was removed under reduced pressure to yield a crude viscous mass that was then delivered slowly into acetone. The precipitate was isolated and collected by vacuum filtration followed by extraction with hot 2-propanol (150 mL). The 2-propanol extracts were concentrated under reduced pressure and a minimal amount of acetone was used to precipitate the product. It was then isolated and dried with vacuum filtration to give 20.5 g (48% yield) of the product as an off-white powder. $^1$H NMR (400 MHz, DMSO-d$_6$): δ 8.60-7.82 (4H, m), 5.79 (1H, s), 5.36 (1H, s) 3.38 (2H, q), 2.89 (2H, t), 1.87 (3H, s). $^{13}$C{$^1$H}NMR (100 MHz, DMSO-d$_6$): δ 168.3, 139.9, 120.4, 38.9, 37.2, 19.1.

Structure 3, FIG. 2A was prepared as follows: In a 10 L round bottom flask, 3-(benzyloxy)-2-methyl-4H-pyran-4-one (230.0 g, 1.0 eq, 1.064 moles) (structure 2, FIG. 2A) was added followed by methanol (2.3 L, 10 vol) and water (2.3 L, 10 vol). This solution was stirred for 5 minutes followed by addition of N-(2-aminoethyl) methacrylamide (structure b, FIG. 2A) (272 g, 2.0 eq, 2.129 mol). After stirring for 5 min, the reaction mixture was charged with 2 M NaOH solution (230 mL, 1 vol) slowly over 10 min. The mixture was then refluxed overnight. After overnight heating, the reaction mixture was cooled to room temperature, and the methanol and water were distilled off under reduced pressure. The semisolid obtained was then diluted with water (5 vol) and the pH was maintained at 7.0 with 2 N HCl. The aqueous layer was then extracted with methylene chloride (3×500 mL). During these extractions an emulsion typically formed which was broken by repeated filtration through celite to separate the organic layer from aqueous layer. The separate organic fractions were pooled and dried with Na$_2$SO$_4$ and then concentrated under reduced pressure to yield a brown semisolid. This material was then slurried in ethyl acetate (3 vol) overnight and filtered to yield light yellow color solid (200 g, 57.5%). $^1$H NMR spectroscopy confirmed the identity of structure 3 of FIG. 2A as N-(2-(3-(benzyloxy)-2-methyl-4-oxopyridin-1(4H)-yl) ethyl) methacrylamide and HPLC confirmed its purity at 96.6%. $^1$H NMR in d$_6$-DMSO (400 MHz) δ 8.11 (bs, 1H), 7.45-7.31 (m, 6H), 6.11 (d, 1H), 5.59 (s, 1H), 5.34 (s, 1H), 4.99 (s, 2H), 3.95 (t, 2H), 3.34 (t, 2H), 2.19 (s, 3H), 1.81 (s, 3H).

Structure 5 of FIG. 2A was prepared as follows. In a 5 L round bottom flask, were charged N-(2-(3-(benzyloxy)-2-methyl-4-oxopyridin-1(4H)-yl) ethyl) methacrylamide (structure 3 of FIG. 2) (200 g; 1.0 eq; 0.612 mol), 11.6 M HCl (10 vol) and the mixture was stirred at RT overnight. After overnight stirring, HCl was distilled off from the reaction mass under reduced pressure. The solid obtained was then dissolved in minimum amount of H$_2$O (5 vol) and a neutral pH (pH 7.0) was attained with 10% NaHCO$_3$ solution (slow addition) upon which a solid precipitated from the solution. The solid was recovered by filtration, washed with cold $H_2O$ on the filter and dried under high vacuum to yield 90 g of a light brown solid representing a 62.1% product yield. $^1$H NMR confirmed identity of the solid as N-(2-(3-hydroxy-2-methyl-4-oxopyridin-1(4H)-yl) ethyl)methacrylamide or also called 3-hydroxy-1-(β-methacrylamidoethyl)-2-methyl-4(1H)-pyridinone (MAHMP) (structure 5, FIG. 2A) and HPLC confirmed a purity of 99.8%. $^1$H NMR in $d_6$-DMSO (400 MHz) δ 8.09 (bs, 1H, NH), 7.37 (d, 1H, ArH), 6.07 (d, 1H, ArH), 5.59 (s, 1H, =CHaHb), 5.33 (s, 1H, =CHaHb), 4.86 (bs, 2H, —OH), 4.01 (t, 2H, —NCH$_2$), 3.37 (t, 2H, —NCH$_2$), 2.28 (s, 3H, —CH$_3$), 1.18 (s, 3H, —CH$_3$) confirmed the structural identity of 3-hydroxy-1-(β-methacrylamidoethyl)-2-methyl-4 (1H)-pyridinone (MAHMP) (structure 5, FIG. 2A).

This example shows the overall yield was much higher with this novel synthesis route being a much improved 62.1% (wt/wt), i.e. approximately 7× greater than the 8.9% (wt/wt) as was obtained for the conventional procedure of Example 1.

Example 3. Measurement of MAHMP in Chelating Compositions

Figure 3:
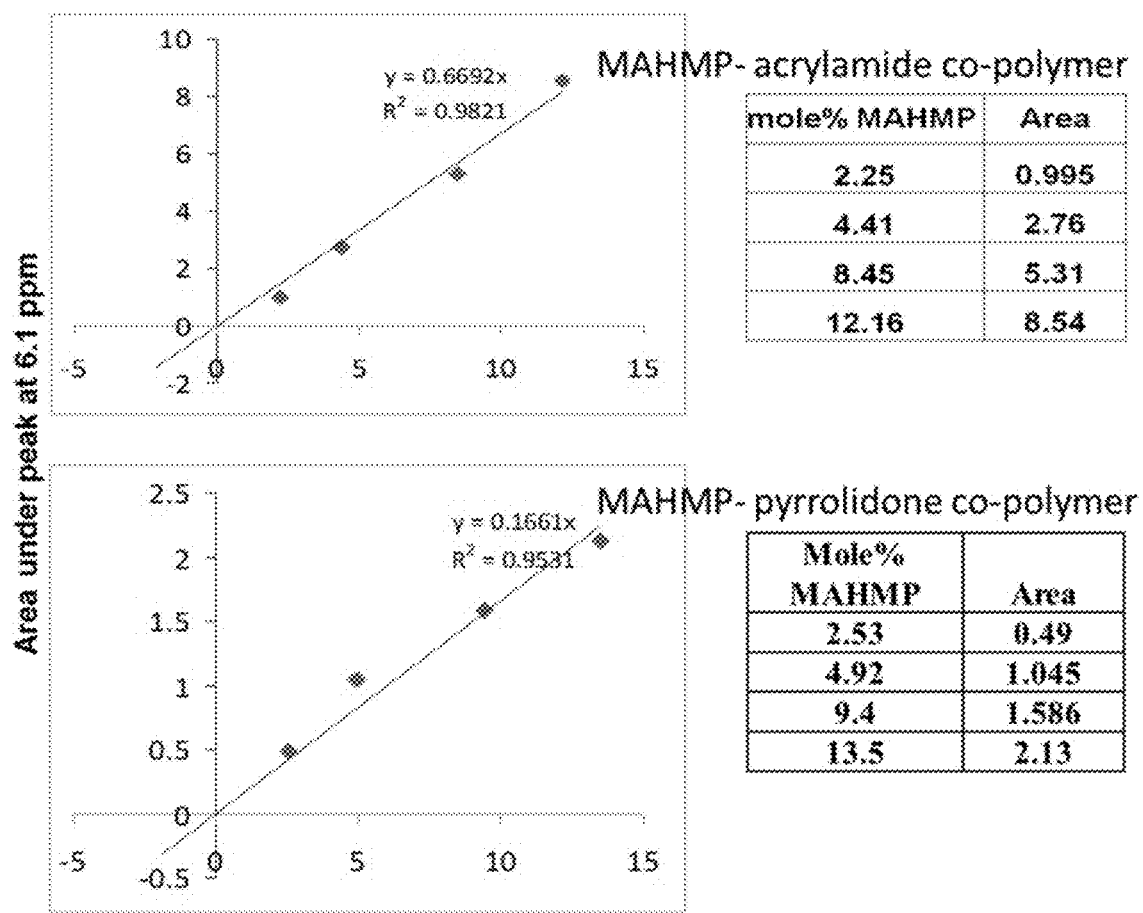
FIG. 3 provides the Proton Nuclear Magnetic Resonance ($^1$H NMR) spectroscopy calibration curves for MAHMP content for MAHMP-acrylamide or -pyrrolidone co-polymer chelating compositions as detailed in Example 3.

Proton Nuclear Magnetic Resonance ($^1$H NMR) spectroscopy was used to estimate 3-hydroxy-1-(β-methacrylamidoethyl)-2-methyl-4(1H)-pyridinone (MAHMP) content of co-polymers as follows. MAHMP prepared as in Example 2 was added at various known concentrations to known quantities of polyacrylamide or polvinylpyrrolidone and the samples were analyzed in deuterated-$d_6$-DMSO for the characteristic MAHMP signal peak at 6.1 ppm relative to the polyacrylamide or polvinylpyrrolidone reference signals This provided calibration curves for MAHMP content for MAHMP-acrylamide or pyrrolidone co-polymer chelating compositions as shown in FIG. 3. The excellent linearity of this calibration curve ($r^2$=0.95 to 0.98) then allowed direct measurement and determination of mol % MAHMP incorporation in either type of co-polymer composition as prepared in Example 4, Example 5, Example 11 and Example 12.

Figure 4:
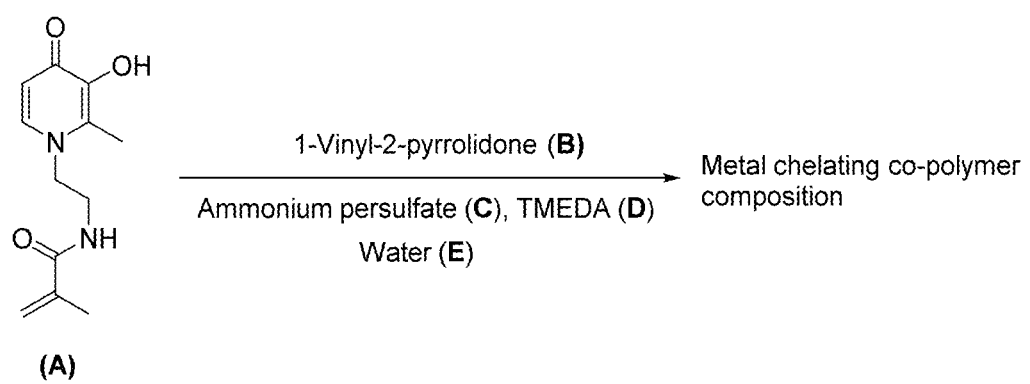
FIG. 4 (prior art) shows the conventional Free Radical Polymerization (FRP) reaction sequence for co-polymer chelating compositions as carried out by the procedure in Example 4.

Example 4; Synthesis of an Aqueous Soluble Co-Polymer Chelating Composition Comprising an Active Pyridinone Metal Binding Group in the Form of MAHMP Co-Polymerized with 1-vinyl-2-pyrrolidone Using FRP Procedures A. Attempts to Optimize Synthesis Attempts to improve utilization of MAHMP, i.e., increase its incorporation into the chelating composition with polymerization using previously disclosed bulk free radical (FRP) procedures were made. These trials were monitored by measurement of residual MAHMP as detectable by Thin Layer Chromatography (TLC) at the end of the polymerization reaction. These trials were also attempts to increase mass yields of the co-polymer product as diagrammed in the reaction sequence shown in FIG. 4. Adjustments to the various chemical reactants (A-E) were as shown in the Table below.

| Reaction Conditions | | | | | |
| --- | --- | --- | --- | --- | --- |
| A (eq) | B (eq) | C (eq) | D (vol) | E (vol) | Observations/Remarks |
| 1 | 21.6 | 0.1 | 0.17 | 85 | 1. Original protocol disclosed in USA patent application publication No. US 2016/0038604 |
| 1 | 21.6 | 0.1 | 0.17 | 42 | 2. Unreacted MAHMP detected by TLC<br>1. Optimization attempt by increasing chemical reactants concentration 2X |
| 1 | 21.6 | 0.1 | 0.17 | 27 | 2. Unreacted MAHMP detected by TLC<br>1. Optimization attempt by increasing chemical reactants concentration 4X |
| 1 | 30 | 0.2 | 0.34 | 85 | 2. Unreacted MAHMP detected by TLC<br>1. Optimization attempt by changing reagents equivalents.<br>2. Unreacted MAHMP not detected by TLC |

The optimized synthesis procedure from above that provided complete consumption of the MAHMP, i.e., no residual detectable by TLC, was then repeated as below.

B. Optimized Synthesis from Adjustment of Reactant Equivalents

To a 3 L flask, water (1.7 L, 85 vol. with respect to (wrt) MAHMP) was charged. Then MAHMP (20 g, 0.0847 mol, 1 eq) was introduced and the reaction mass stirred for 10 min to give a clear solution. This solution was then heated to 50° C. 1-Vinyl-2-pyrrolidone (NVP) (271 mL, 2.54 mol, 30 eq wrt to MAHMP) was then charged drop wise using an addition funnel. After completion of the addition heating was stopped and the mixture cooled to RT over 1 h. Ammonium persulfate (3.86 g, 0.0167 mol, 0.2 eq wrt to MAHMP) was then added and the resulting clear solution was flushed with nitrogen for 20 min. TMEDA (6.8 mL, 0.34 vol. with respect to MAHMP) was then added drop-wise over 15 min and the polymerization was carried out for 2 h at 40° C. After 2 h heating the reaction was stopped and the reaction mass was then cooled to RT over 1 h. The resulting polymer solution (1.98 L) was enclosed in a visking dialysis bag and dialyzed against distilled water (100 L) for 48 h which involved ten changes of water at 5 h intervals. After dialysis, the solution (3 L) was divided in two fractions A and B (1.5 L each). Fraction A was lyophilized while Fraction B was azeotrope treated using toluene (7 L) to remove water. The combined yield of the pale yellow to faint orange tinged co-polymer metal chelating composition A+B was 20.6 g representing a mass yield of only 7% with respect to the combined total masses of the MAHMP and NVP utilized. Analysis of this composition (reference number P315-A00279-029) for its MAHMP content using the procedure of example 3 indicated a MAHMP content of 21.4% (w/w) This example illustrates a yield and synthesis efficiency problem in that to ensure more complete MAHMP incorporation into the co-polymer composition excess NVP had to be utilized resulting in a large excess of free unreacted NVP. This problem was overcome by utilizing RAFT synthesis procedures as described in Example 12 below.

C. Optimized Typical FRP Synthesis Procedure to Obtain High Molecular Weight (Batch No. IS09758-045)

FRP procedures were found useful for obtaining a relatively high molecular weight of the MAHMP-pyrrolidone co-polymer as would be desirable for some uses of the resulting metal chelating co-polymer compositions, for example where a higher molecular weight material as applied to a wound site or onto a mucosal surface such as the outer ear or vagina would be retained for longer periods of time for activity, i.e., as compared to lower molecular weight material that would diffuse away and be cleared more quickly from the site of application. This example illustrates means for obtaining such a higher molecular weight MAHMP-pyrrolidone co-polymer material by prolonging reaction times (18 h versus 2 h) of the FRP polymerization at increased reaction temperature (70° C. versus 40° C.). The procedure below makes reference to the reaction components of FIG. 4.

In a 3-neck, 50 mL round bottom flask, equipped with a magnetic stirrer, reflux condenser (0.5 g, 0.0021 mol) MAHMP (A) and (7.05 g, 0.063 mol) N-Vinyl-2-pyrrolidone (NVP) (B) were dissolved in 26 mL of deionized water (portion of E) and the mixture was stirred for 20 min under $N_2$. Then, (0.49 g, 0.0042 mol) tetramethylethylenediamine (accelerator) (D) was added and resultant mixture was degassed by purging it with $N_2$ for 20 min. Post degasification, (0.48 g, 0.0021 mol) ammonium persulfate (initiator) (C) in 4 mL degassed DI water (balance of E) was added to the flask. Thereafter, the mixture was heated slowly to 70° C. over 30 min and the reaction was continued at the same temperature for 18 h under $N_2$. After 18 h, the reaction mass was tested and it was determined that no detectable residual unreacted (non-polymerized) MAHMP was present but residual NVP was present as measured by Thin Layer Chromatography (TLC). The mixture was placed on a rotary evaporator to remove water at 50° C. under reduced pressure (35-50 mmHg). The crude mass was dissolved in methanol and filtered to remove any insoluble impurities. The filtrate was concentrated to approximately 50 weight % polymer solution (e.g., approximately 8.5 g crude co-polymer product mass in an equal volume of methanol) and this solution was slowly precipitated in 50 (volumes) excess MTBE (Methyl Tertiary Butyl Ether) under constant stirring. Thereafter the precipitate was filtered, washed with MTBE and dried on a rotary evaporator at 50° C. under reduced pressure (35-50 mmHg) for 4-6 h, until a constant weight was observed. The co-polymer product (sample ISO9758-045) yield was 42% relative to the combined starting mass of MAHMP and NVP.

Figure 5:
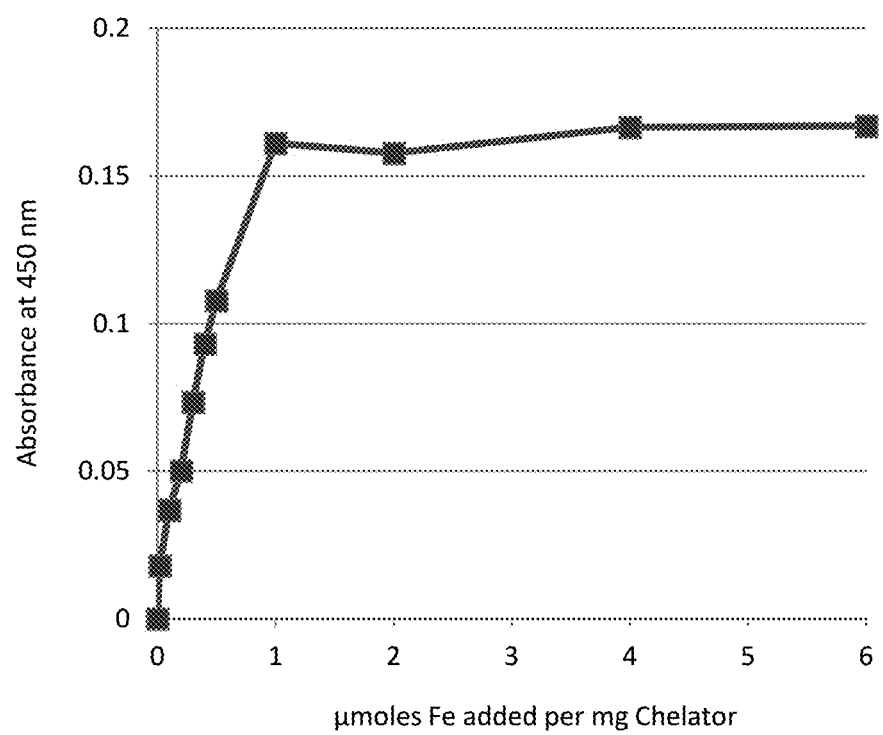
FIG. 5 is a graph of the data obtained when measuring iron binding characteristics of a chelating co-polymer composition as described in the procedure of Example 5.

Example 5: Characterization of Chelating Co-Polymer Compositions as to Iron Binding Activity Known weights of samples of metal chelating co-polymer compositions were dissolved in water at neutral pH and reacted with excess iron citrate solution for a minimum of 2 h at ambient temperature and the red color that developed through interaction of the iron with the polymer-contained MAHMP was measured at 450 nm in a spectrophotometer. Standards of varying known amounts of iron reacted with free MAHMP were used to confirm the red color was directly attributable to the binding of iron by MAHMP as incorporated into the co-polymer composition. A saturation curve as shown in FIG. 5 was prepared for the iron chelating co-polymer composition as shown for the composition prepared as in Example 4(B). From this the relative iron binding capacity of the composition was determined as the amount of iron providing the maximum absorbance at 450 nm and with little change upon further ion addition. On this basis, the composition prepared as in Example 4 (B) had an iron capacity of approximately 1 umol Fe/mg composition. This example shows the iron dose dependent development of a measurable chromophore that absorbs light at 450 nm as characteristic of the chromophores produced with hydroxylpyridinones when these bind iron. Therefore this demonstrates that MAHMP was incorporated into the co-polymer and that the MAHMP so incorporated binds iron.

Example 6: Characterization of Chelating Co-Polymer Compositions as to Biological Activity Chelating compositions were assessed for their biological activity in vitro by determination of their growth inhibitory activity for *Staphylococcus aureus* (strain 038, a clinical isolate from a corneal infection obtained from Dr. Mark Wilcox, University New South Wales, Australia or strain ATCC 43300, a prototypical clinical isolate and reference strain obtained from the American Type Culture Collection) and *Candida albicans* (SC5314, a prototypical clinical isolate and reference strain obtained from the American Type Culture Collection or strain 3969 a clinical isolate obtained from the Queen Elizabeth II hospital, Halifax, Canada). The microorganisms were grown in RPMI 1640 culture medium and tested in fresh aliquots of RPMI 1640 medium or in medium that had been partially deferrated by the method of Holbein and Mira (Holbein B. E, Mira de Orduña R. 2010, FEMS Microbiol Lett. 307(1):19-24, herein incorporated by reference) to allow testing at low Fe levels or with iron re-added at known concentrations to this deferrated medium. Growth at 30° C. was measured by optical density when the test samples were incubated in tubes or visually when growth was tested in microtitre dish wells. The results in the table below show the inhibitory activities (expressed as Minimum Inhibitory Concentration (MIC) suppressing growth completely over a 48 h incubation period) for the metal chelating composition as prepared in Example 4 (B) and (C). The results show the compositions inhibit growth and also show that the degree of inhibition is related to the amount of iron available in the growth medium, higher amounts reducing the inhibitory activity of the metal chelating compositions. The results thus confirm the activities of the metal chelating compositions were related to their iron chelating activities and that iron as in the culture medium as bound by the compositions denied iron as needed for microbial growth for both a pathogenic bacterium and a pathogenic fungal yeast.

| Chelating Composition | Fe in medium μM | S aureus MIC μg/mL | C albicans MIC μg/mL |
|---|---|---|---|
| P315-A00279-029 | 0.05 | 0.5 | <0.25 |
|  | 0.15 | 2.0 | 4.0 |
| ISO 9758-045 | 0.05 | 0.5 | 0.5 |
|  | 0.15 | 1.0 | 32 |

Figure 6:
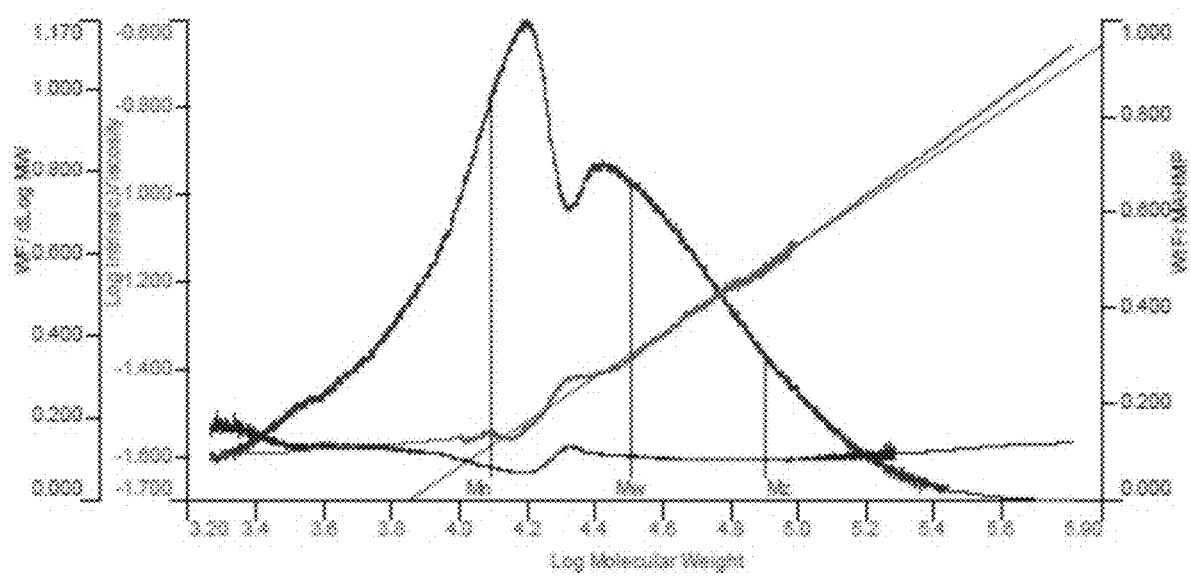
FIG. 6 is a graph of the data obtained from the characterization of chelating co-polymer compositions showing physical characteristics including relative molecular weight as described in Example 7.

Example 7: Characterization of Chelating Co-Polymer Compositions as to Physical Characteristics Including Relative Molecular Weight Chelating compositions were analyzed by Gel Permeation Chromatography (GPC) using a Polymer Laboratories PLGPC 50 instrument by the following methods. Samples were dissolved at 2.5 mg/mL in either in dimethylformamide for non-aqueous separations or in 0.2 M sodium nitrate in water for aqueous separations. For non-aqueous separations the sample (50 uL) was applied to a Jordi DVB mixed bed and eluted with dimethylformamide at a flow rate of 0.8 mL/min at 50° C. Narrow range polymethymethacrylate standards of known molecular weight were used to calibrate the system and samples were analyzed for relative molecular weight (Mn and Mw) and also polydispersion index PDI (Mw/Mn). For aqueous separations (100 uL) was applied to a PL-aquagel mixed OH30 bed and eluted with 0.2 M sodium nitrate in water at 30° C. at a flow rate of 1.0 mL/min. Narrow range polvinylpyrrolidone (PVP) standards of known molecular weights were used to calibrate the aqueous separations for determinations of Mn, Mw and PDI (Mw/Mn). This relative GPC analysis showed a relatively broad distribution of molecular weights with a measured Poly Dispersion Index PDI for this composition of 2.4 while a PDI of <1.5 would indicate a narrow distribution. It is well understood that the free radical polymerization processes usually result in broader distributions of molecular weights. Relative GPC analysis of this sample also indicated an average molecular weight (Mw) of just 3.7 kDa but this was found to be much higher when the composition's true molecular weight was measured by laser light scattering using the alternate GPC method as described in Example 13 and as shown in FIG. 6. By this alternate GPC method the PDI for this sample was also found to be 2.4 and the broad MW distribution with relatively high molecular weights can be seen in FIG. 6. Laser light scattering measurement indicated a true MW (ave) for this sample of 32 kDa, i.e., approximately 10× the value as was inferred by relative GPC analysis, i.e., in comparison to PVP standards. This example illustrates the very broad distribution of molecular weights of chelating compositions prepared from bulk free radical polymerization techniques.

Figure 7:
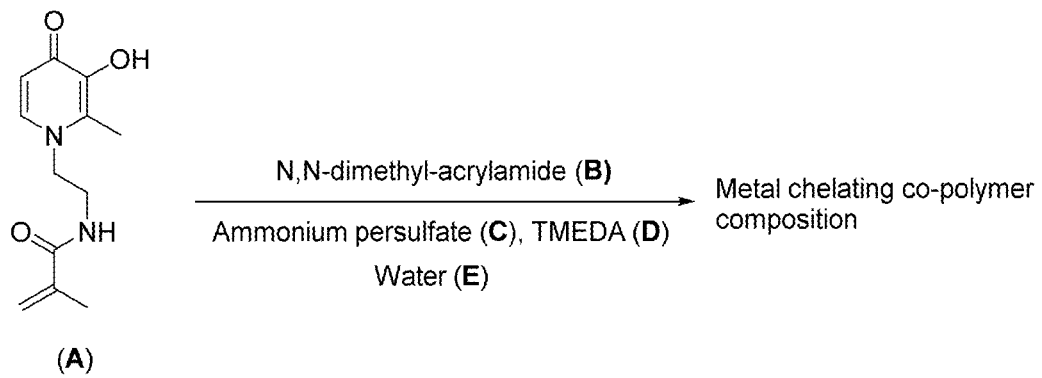
FIG. 7 (prior art) is a synthesis scheme for metal chelating acrylamide co-polymer compositions using the FRP process as described in Example 8.

Example 8; Synthesis of an Aqueous Soluble Co-Polymer Chelating Composition Comprising an Active Pyridinone Metal Binding Group in the Form of MAHMP Co-Polymerized with Methyl Acrylamide Using FRP Procedures This co-polymer when prepared by bulk FRP chemical procedures as shown in FIG. 7 presented yet a different problem to those encountered for the pyrrolidone containing co-polymer described in Example 4 above. Polymerization of these acrylamide containing compositions was rapid and often resulted in a solid gel material of very high molecular weight such that these were not water soluble, instead of the desired water soluble co-polymer compositions sought.

A. Attempts to Optimize Synthesis

The general FRP synthesis procedure for co-polymer compositions containing MAHMP and acrylamide is provided below with reference to the chemical components shown in FIG. 7.

MAHMP, 3-hydroxy-1-(β-methacrylamidoethyl)-2-methyl-4(1H)-pyridinone (A) (2.5 mmol, 0.59 g), prepared as in Example 2, was dissolved in 50 mL water (E) in a 250 mL flask with a mechanical stirrer at 50° C. N, N-dimethylacrylamide (B) (54 mmol, 5.6 mL) was added while stirring and the mixture was cooled to room temperature. Ammonium persulfate initiator (C) (0.057 g) was added and after the flask was flushed with nitrogen for 20 minutes, N,N,N', N'-tetramethylethylenediamine accelerator (TMEDA) (D) (0.1 mL) was added and the polymerization was carried out for 2 h at 40° C. The polymer solution was observed as to solubility and freedom from gel formation. This procedure almost always resulted in gel formation within the 2 h polymerization procedure or during the addition phase of the TMEDA (D). Various reaction conditions were varied in separate trials, including separate trials of homo-polymerization of acrylamide, i.e., without inclusion of MAHMP (A), to observe if gel formation could be avoided. Changes to the temperature used for the polymerization reaction from 40° C. to as low as 5° C. all still typically resulted in gel formation during the addition phase for the TMEDA accelerator. Changes to the concentrations of the reactants by adjustment of the amount of water (E) or the stoichiometric ratios of initiator (C) and accelerator (B) were not found useful to avoid gel formation. Surprisingly, gel formation was avoided by changing the order of addition of initiators (C) and accelerator (D) as described below.

B. Optimized Synthesis by Reverse Addition of APS and TMEDA

Figure 8:
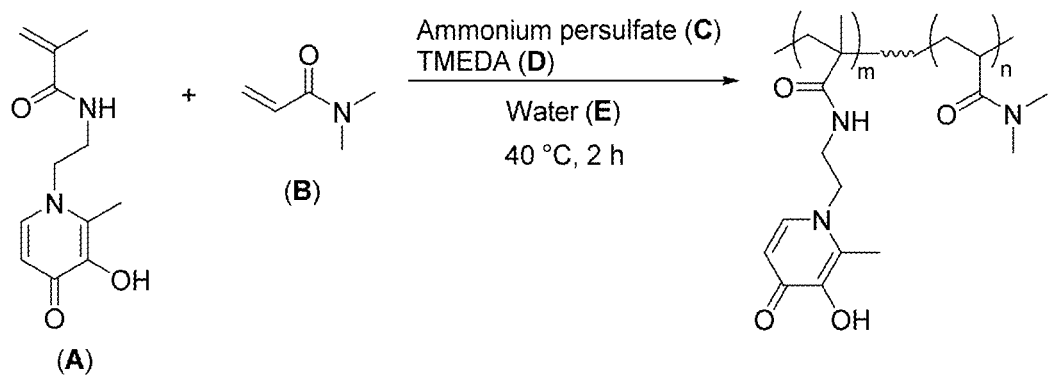
FIG. 8 is a synthesis scheme for metal chelating acrylamide co-polymer compositions using the FRP process with reverse addition of polymerization accelerator agent TMEDA being added before the chemical initiator APS as described in Example 9.

The optimized FRP process synthesis for MAHMP and acrylamide co-polymer composition batch No. IS09732-047 is described below and with reference to the chemical components A through E shown in FIG. 8. Here the polymerization accelerator agent TMEDA (D) was added before the chemical initiator APS (C).

In a 3-neck, 250 mL round bottom flask, equipped with a magnetic stirrer (2.5 g, 0.025 mol) N,N'-dimethylacrylamide (DMA) (B), (0.55 g, 0.0023 mol) MAHMP (A) were dissolved in 140 mL of deionized water (portion of E) and the mixture was stirred for 20 min under $N_2$. To this mixture (0.15 g, 0.00129 mol) TMEDA accelerator (D) in 5 mL deionized water (portion of E) was added and the total mixture was degassed by purging with $N_2$ for 20 min. Post degasification, (0.105 g, 0.00046 mol) ammonium persulfate (initiator) (C) in 5 mL degassed water (portion of E) was added gradually to the stirring mixture in the flask over 30 mins. Thereafter, the mixture was heated slowly to 40° C. over 30 min and the reaction was continued at the same temperature for 2 h under $N_2$. After 2 h, the reaction mass was placed onto a rotary evaporator to remove water under reduced pressure (35-50 mmHg). The crude dewatered mass was dissolved in methanol and filtered to remove any insoluble impurities. The filtrate was concentrated to approximately 50 weight % and this polymer solution was slowly precipitated in excess Methyl Tertiary-Butyl Ether (MTBE) under constant stirring. Thereafter the precipitate was filtered and dried in a flask on a rotovapor at 50° C. under 35-50 mmHg for 4-6 h, until constant weight and the white to pale yellow product co-polymer was obtained. This example also illustrates an important alternative to dialysis and lyophilization to recover the dry co-polymer product as this co-polymer composition was purified and recovered by MTBE precipitation. The combined yield of co-polymer metal chelating composition was 2.6 g representing a mass yield of 85% with respect to the combined total masses of the MAHMP and DMA supplied to the polymerization reaction. The characteristics of this chelating co-polymer composition are summarized in the table below. The MAHMP content of this chelating composition determined by the method described in example 3, its iron binding characteristics were determined as in example 5, and its biological activity was determined as in example 6. GPC analysis for molecular weights Mn and Mw and PDI were determined by the method of Example 7. The composition was found to bind iron and sequester its availability for *S. aureus*. This example shows that reverse addition of initiator and accelerator did provide better control of the polymerization avoiding gel formation and provided a composition of relatively high MW and with high yield. However the PDI was >2.5 and thus this Mw distribution of the product composition chains was fairly broad and this thus illustrates one of the problems in using FRP synthesis chemistry. A narrow MW distribution, i.e., lower PDI, would be advantageous for producing a metal chelating co-polymer composition.

| Characteristic | Result |
| --- | --- |
| Color | White-pale yellow |
| MAHMP content | 6.3 mol % |
| Iron loading | 2 µmol/mg |
| MIC low Fe RPMI S. aureus | 0.25 µg/mL |
| MIC RPMI control S. aureus | 8 µg/mL |
| Mn | 285270 |
| Mw | 758020 |
| PDI (Mw/Mn) | 2.65 |

Example 9: Preparation of RAFT Agents Suitable for Synthesis of a Soluble Co-Polymer Chelating Composition Comprising an Active Pyridinone Metal Binding Group Co-Polymerized with Vinyl-Pyrrolidone or Methyl-Acrylamide Using RAFT Procedures On the basis of preferring aqueous RAFT polymerization procedures the selection of candidate RAFT agents was narrowed and examples were prepared in the laboratory according to the reaction schemes of FIG. 9 and as described below.

RAFT-3: 2-Ethoxythiocarbonylsulfanyl-Propionic Acid Ethyl Ester (ETSPE)

In a 2-neck 50 mL round bottom flask (5 g, 0.0312 mol) potassium ethyl xanthate and ethyl-2-bromo propionate (6.2 g, 0.0343 mol) were added. To this mixture 20 mL ethanol was added and the reaction mass was stirred for 12 h at RT under a nitrogen atmosphere. The white precipitate (KBr) as formed during the reaction mixture was filtered off and the filtrate was diluted with 150 mL of ether. The ether solution was washed with DI water 4×20 mL, dried over anhydrous sodium sulfate and placed on a rotary evaporator at 30° C. under reduced pressure (0.075 mmHg) to remove residual water and obtain a yellow liquid. This liquid was purified by column chromatography on silica gel using Hexanes/Ethyl acetate (95:5) elution to obtain the oily yellow liquid product, 2-Ethoxythiocarbonyl sulfanyl-propionic acid ethyl ester (ETSPE).

RAFT-4: 2-Ethoxythiocarbonylsulfanyl-2-Methyl-Propionic Acid (ETSPA)

In a 2-neck, 50 mL round bottom flask (5.27 g, 0.0329 mol) potassium ethyl xanthate and 2-bromoisobutyric acid (5.0 g, 0.0299 mol) were taken. To this mixture 14 mL deionized water was added and the turbid yellow solution was stirred for 48 h at RT under a nitrogen atmosphere. After the reaction, the water layer was acidified with approximately 6 mL concentrated HCl and extracted twice with 40 mL diethyl ether. The combined ether fraction of approximately 80 mL was dried over anhydrous sodium sulfate and then placed on a rotary evaporator at 30° C. under reduced pressure (0.075 mmHg) to obtain a yellow liquid. The yellow oily residue was recrystallized on cooling to 0° C. Thereafter the crystals were washed with petroleum ether, the solid was again dissolved in ethanol and then re-crystallized with the addition of deionized water. These crystals were filtered and dried under high vacuum as product 2-ethoxythiocarbonylsulfanyl-2-methyl-propionic acid (ETSPA).

RAFT-5: Poly-DMA Macro-CTA (Targeted Degree of Poly-Acrylamide Polymerization of 15)

To a 50 mL, round-bottom flask equipped with a magnetic stir bar and septum adapter were added N,N-Dimethylacrylamide (DMA) (5 g, 0.05 mol), 4-cyano-4-[(dodecylsulfonylthiocarbonyl)sulfanyl]pentanoic acid (CTA) (0.8134 g, 0.002 mol), azobisisobutyronitrile (AIBN) (0.108 g, 0.00066 mol) and dioxane 15 mL. The reaction mixture was allowed to dissolve and then purged with argon to degas the polymerization mixture. The flask was then sealed with a rubber septum and heated for 4 h at 60° C. The crude polymer was precipitated into excess of MTBE re-dissolved into methanol and precipitated again with an excess of MTBE. Thereafter the precipitate was filtered and dried on a rotovapor at 50° C. under reduced pressure (35-50 mmHg) for 4-6 h, until constant weight was obtained for the product poly-DMA macro-CTA.

The above RAFT agents were selected as examples for testing as these were readily soluble in water. It should be noted that non-aqueous RAFT polymerization schemes using RAFT agents that are of low water solubility but are soluble in organic systems are also possible and capable of yielding chelating compositions that, after their recovery from the non-aqueous synthesis medium, are sufficiently soluble in aqueous systems for their intended uses as disclosed herein.

Example 10: Testing of RAFT Agents for Suitability for Controlling Polymerization and Resultant Co-Polymer MW RAFT agents 3 and 4 were first tested for their abilities for directing aqueous polymerization using a homo-polymerization of acrylamide by the following procedure. Additional RAFT agents tested included commercially available 4-cyano-4-[(dodecyl sulfanylthiocarbonyl)sulfanyl]pentanoic acid (CTA termed RAFT-1 for the testing below) and bis(carboxymethyl)trithiocarbonate (termed RAFT-2 for the testing below). Each RAFT agent was compared for polymerization of dimethyl acrylamide (DMA) using the same stoichiometric ratios of DMA:RAFT:APS:TMEDA. Results of these RAFT mediated acrylamide homo-polymerization tests are summarized in the table below.

| Test Batch no. | RAFT agent | Reactant molar ratios [DMA]:[RAFT]:[APS]:[TMEDA] | Molecular Weight by GPC | | |
| --- | --- | --- | --- | --- | --- |
| | | | Mn | Mw | PDI Mw/Mn |
| IS09758-017 | RAFT-1 | 142:1:2.8:1.7 | RAFT agent insoluble; high molecular weight insoluble gel formed | | |
| IS09733-22 | RAFT-2 | 142:1:2.8:1.7 | Very Broad distribution; too large for GPC analysis | | |

-continued

| Test Batch no. | RAFT agent | Reactant molar ratios [DMA]:[RAFT]:[APS]:[TMEDA] | Molecular Weight by GPC | | PDI Mw/Mn |
|---|---|---|---|---|---|
| | | | Mn | Mw | |
| IS09733-13 | RAFT-3 | 142:1:2.8:1.7 | 18405 | 26860 | 1.45 |
| IS09733-21 | RAFT-4 | 142:1:2.8:1.7 | 22205 | 30515 | 1.37 |

These results confirmed that RAFT agents that are not soluble in water are not useful for aqueous RAFT polymerization. Note again, the above RAFT agents were selected as examples for testing as these were readily soluble in water. It should be noted that non-aqueous RAFT polymerization schemes using RAFT agents that are of low water solubility but are soluble in organic systems are also possible and capable of yielding chelating compositions that, after their recovery from the non-aqueous synthesis medium, are sufficiently soluble in aqueous systems for their intended uses as disclosed herein. In addition, the conventional agent RAFT-2, bis(carboxymethyl)trithiocarbonate resulted in a very broad MW distribution of the acrylamide polymer indicating it was not suitable for the intended co-polymer composition syntheses. Both RAFT-3 and RAFT-4 provided efficient polymerization to form a polymer product of sufficiently low MW, i.e., approximately 30 kDa or less, so as to retain its water solubility. Both RAFT agents also provided fairly narrow MW distributions (PDI≤1.45) indicating both of these RAFT agents had potential for co-polymerization syntheses with MAHMP-acrylamide or MAHMP-pyrrolidone co-polymers.

Figure 10A:
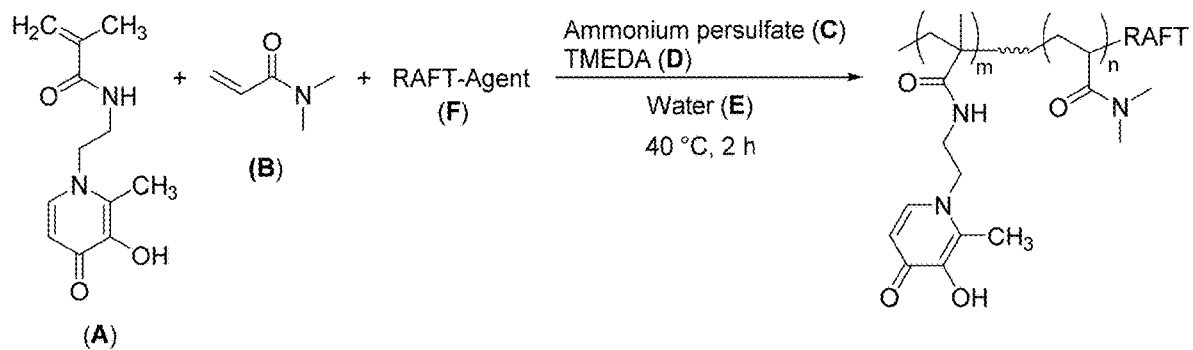
FIGS. 10A and 10B show chemical synthesis schemes for the metal chelating compositions MAHMP-acrylamide co-polymer (FIG. 10A) and MAHMP-pyrrolidone co-polymer (FIG. 10B) using RAFT polymerization procedures as described in Example 11.

Example 11: Synthesis of a Co-Polymer Chelating Composition Comprising an Active Pyridinone Metal Binding Group in the Form of MAHMP Co-Polymerized with Dimethyl Methyl Acrylamide Using RAFT Procedures A. Typical RAFT Polymerization Procedure The synthesis (Batch no. IS09758-031) makes reference to the reactants shown in FIG. 10 (A). In a two-neck 50 mL round bottom flask, equipped with a magnetic stirrer (4.0 g, 0.4035 mol) N,N'-dimethylacrylamide (B) and (0.44 g, 0.0018 mol) MAHMP (A) were dissolved in 10 mL of deionized water (portion of E) and the mixture was stirred for 20 min under $N_2$. To this mixture RAFT agent RAFT-4 (0.011 g, 5.27E-5 mol) (F) and (0.010 g, 8.96E-5 mol) tetramethylethylenediamine (D) (accelerator) were added and the mixture was degassed by purging with $N_2$ for 20 min. Post degasification, ammonium persulfate initiator (C) (0.034 g, 1.47E-4 mol) was added to the reaction mixture. Thereafter, the mixture was heated to 40° C. and the reaction was continued at the same temperature for 18 h under $N_2$. After 18 h, the reaction mass was placed on a rotary evaporator under reduced pressure to remove water. The crude mass was dissolved in methanol and filtered to remove any insoluble impurities. The filtrate was concentrated to a polymer solution of approx. 50 wt % and this solution was slowly precipitated in 50 volumes excess MTBE (Methyl Tert-Butyl Ether) under constant stirring. Thereafter, the precipitate was filtered and dried on a rotary evaporator at 50° C. under 35-50 mmHg for 4-6 h, until constant weight was observed to yield the white to faint yellow product MAHMP-acrylamide copolymer sample IS09758-031.

B. Comparison of Different RAFT Agents

The above synthesis procedure was repeated but with alternate RAFT agents to establish which RAFT agent might provide the highest level of control of product molecular weight from conversion of monomers (A) and (B) to co-polymer product. The characteristics of the resulting co-polymer compositions were compared to those of batch ISO9758-031 a prepared in Example 11A above. These tests showed similar performance for RAFT-3 and RAFT-4 but RAFT-5 was less useful for ensuring MAHMP utilization. RAFT-3 and RAFT-4 mediated MAHMP incorporations into co-polymer was >70% of the MAHMP supplied to the polymerization reactions but this incorporation declined to <60% in the case of the RAFT-5 mediated co-polymer product. These results indicated RAFT-3 and RAFT-4 to be preferred RAFT agents for preparation of water-soluble MAHMP-acrylamide co-polymer cheating compositions. The resulting co-polymer compositions were soluble in water and had average molecular weights (Mw) of around 20 kDa in the case of RAFT-3 or RAFT-4 mediated polymerizations. The Mw was also substantially lower in the case of RAFT-5 mediated polymerizations.

| Batch no. | RAFT Agent | [DMA + MAHMP]: [RAFT]: [APS]: [TMEDA] | MAHMP incorporated mol % in product [% of supplied] | GPC | | |
|---|---|---|---|---|---|---|
| | | | | $M_n$ | $M_w$ | PDI $M_w/M_n$ |
| IS09758-026 | RAFT-3 | 800:1:2.8:1.7 | 3.27% [74%] | 10792 | 21354 | 1.97 |
| IS09758-031 | RAFT-4 | 800:1:2.8:1.7 | 3.12% [71%] | 8651 | 18317 | 2.11 |
| IS09758-028 | RAFT-5 | 800:1:2.8:1.7 | 2.51% [57%] | 9592 | 12811 | 1.33 |

C. Optimization to Achieve Higher Molecular Weight of MAHMP-Acrylamide Co-Polymer A series of polymerization tests were performed with RAFT-4 mediated co-polymerizations of MAHMP and acrylamide using the synthesis procedure detailed in A above but with a modified introduction of the MAHMP. MAHMP was found to interfere with polymerization possibly related to its chemical abilities to accept radicals needed for polymerization progress and therefore interfere by early termination of the growing co-polymer chain. The synthesis procedure as above (A) was performed except that MAHMP was not added to the initial reaction mixture. Rather, the MAHMP was introduced during the actual polymerization by two methods. In one test one half of the MAHMP was added initially as in the procedure of A above and the other half was added one minute after the start of polymerization. In a second test, the MAHMP was separately dissolved in a portion of the water used along with the DMA, this was degassed and then this MAHMP/DMA mixture was added in two equal portions. The first portion was added 0.5 h after starting the reaction and the second portion was added at 1 h. This technique of sequential introduction of MAHMP in solution was also tested at a different ratio of reactants. The results of these tests are shown in the table below. Solid MAHMP addition resulted in very low MAHMP incorporation in the co-polymer as can be observed for batch IS09733-26 and this was likely caused by system heterogeneity. MAHMP added as a solution also containing the DMA, i.e. as a solubilized mixture added to the system in two portions provided improved incorporation of MAHMP at two different ratios of DMA to MAHMP as was observed for batches IS09865-007 and IS09865-006) where 60% MAHMP incorporation was determined in the resulting copolymers. These observations indicated the inhibiting effect of MAHMP in the system can be reduced by lowering its effective concentration during the course of polymerization by adding a portion of the MAHMP during the polymerization process as opposed to all at the imitation of polymerization.

min under $N_2$. To this mixture (0.136 g, 0.000652 mol) RAFT Agent, 2-ethoxythiocarbonylsulfanyl-2-methyl-propionic acid (ETSPA) (F) and (0.227 g, 0.0.00195 mol) TMEDA (accelerator (D)) were added and the total mixture was degassed by purging $N_2$ for 20 min. Post degasification, tertiary butyl hydroperoxide (0.35 g, 0.00388 mol) (initiator (C)) was added to the mixture. Thereafter, the mixture was heated to 40° C. and the reaction was continued at the same temperature for 18 h under $N_2$. After 18 h, the reaction mass was placed on a rotary evaporator to remove water under reduced pressure. The crude mass was dissolved in methanol and filtered to remove any insoluble impurities and the filtrate was concentrated to approximately a 50 weight % polymer solution. This solution was then slowly precipitated with 50 volumes excess MTBE under constant stirring. Thereafter the precipitate was filtered and dried on a rotary evaporator at 50° C. under 35-50 mmHg for 4-6 h, until constant weight of product co-polymer (batch IS09865-025) was observed. The mass yield of the MAHMP-pyrrolidone co-polymer was 80% with respect to the mass of the monomers (A+B) initially supplied to the polymerization reaction and the co-polymer was found to contain a 5.7% MAHMP content as determined by $^1$H NMR spectroscopy using the method of Example 3. The metal chelating co-polymer was found to have a molecular weight (Mw) of 7.3 kDa with a PDI (Mw/Mn) of 1.7 using the GPC analysis methods of Example 7. The biological activity of this co-polymer showed an MIC of 2 g/mL for both *S. aureus* and *C. albicans* when tested using the methods of Example 6.

Alternatively, in a further embodiment, the benzyl ether hydroxyl protecting group may be removed post-polymerization by treating the crude polymer mass, following the removal of water, with an excess amount of concentrated

| Batch no. | [DMA + MAHMP]: [RAFT-4]: [APS]: [TMEDA] | Time (h) | MAHMP addition technique | MAHMP Incorp. mol % [% added] | Molecular weight distribution by GPC | | |
|---|---|---|---|---|---|---|---|
| | | | | | $M_n$ | $M_w$ | PDI $M_w/M_n$ |
| IS09733-26 | 800:1:2.8:1.7 | 18 | Solid MAHMP added in two portions; 0.5 h and 1 h | <1% | 91245 | 212992 | 2.3 |
| IS09865-007 | 800:1:2.8:1.7 | 18 | MAHMP/DMA mixture added in two portions; 0.5 h and 1 h | 2.65% [60%] | 71876 | 205488 | 2.85 |
| IS09865-006 | 250:1:2.8:1.7 | 18 | MAHMP/DMA mixture added in two portions; 0.5 h and 1 h | 2.64% [60%] | 22561 | 127287 | 5.6 |

Example 12: Synthesis of a Soluble Co-Polymer Chelating Composition Comprising an Active Pyridinone Metal Binding Group in the Form of MAHMP Co-Polymerized with Vinyl-Pyrrolidone Using RAFT Procedures A. Typical Optimized RAFT Polymerization Procedure This example (Batch no. IS09865-025) shows generally optimized synthesis conditions in terms of obtaining high yield conversion of monomers to co-polymer product and in reference to FIG. 10 B. Into a two-neck 50 mL round bottom flask, equipped with a magnetic stirrer and a reflux condenser (3.5 g, 0.0315 mol) N-vinyl-2-pyrrolidone (B) and (0.25 g, 0.00106 mol) MAHMP (A) were dissolved in 4 mL of deionized water (E) and the mixture was stirred for 20

HCl. The resultant solution may then be left to stir at room temperature whereby the degree of protecting group removal is monitored by collecting $^1$H NMR spectra of successive aliquots of the polymer solution over time. Upon complete removal of protecting group, the pH of the solution may be adjusted to neutral by using 10% $NaHCO_3$ and the polymer mass precipitated by adding an excess amount of acetone. The crude mass may then be collected and dissolved into methanol where the steps to purify the polymer would be continued as described above.

B. Testing of Alternative Initiator for Polymerization

The relative efficiencies of two different initiator systems for co-polymerization were compared. This included APS as was found useful for FRP synthesis of the MAHMP-pyrrolidone co-polymer compositions as described in Example 4 as compared to the initiator Tertiary Butyl HydroPeroxide (TBHP) as was utilized as in example A above. The results of these tests are shown in the table below. Both tests employed the same reaction procedure as in A above (i.e., ratio MAHMP (A):NVP (B) of 1:30). Initiator (C) TBHP was replaced with Ammonium Persulfate (APS) for batch IS09758-062.

| Batch no | Reaction Conditions | | | | MAHMP Content | Remarks |
|---|---|---|---|---|---|---|
| | (F) (eq) | (C) (eq) | (D) (eq) | (° C.) | mol % (NMR) | |
| IS09865-025 | 1 | TBHP 6 | 3 | 40 | 5.7 | Yield = 90%, Mw-7298 PDI = 1.71 |
| IS09758-062 | 0.61 | APS 0.61 | 1.86 | 70 | 19.75 | Yield = 12%, Mw-24555 PDI = 12 |

Low overall yield was observed when the APS initiator was used and the co-polymer was of higher Mw with increased MAHMP content.

C. Optimization of MAHMP:NVP Monomer Ratio

Figure 10B:
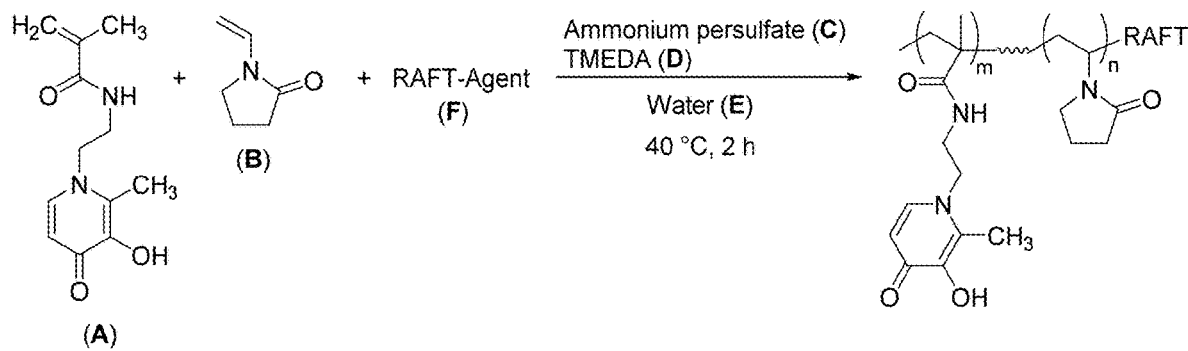

In reference to FIG. 10B, a series of test polymerizations were carried out using the procedure of Example A (above) except that the ratio of metal cheating monomer MAHMP (A) to the co-monomer NVP (B) was varied while retaining the overall total monomer (A+B) content at 50 equivalents to the polymerization reaction and while maintaining the other chemical components (C), (D), (E) and (F) the same for each trial. The results in the table below showed that as the amount of MAHMP (A) supplied for polymerization was increased relative to NVP (B) the overall co-polymer yield decreased but the proportion of MAHMP content in the product co-polymer increased. Ideally a co-polymer MAHMP content of 10-20% might be preferred for a chelating co-polymer composition in relation to it having high metal binding capacity, However, retaining high co-polymer yield is also very important for efficiency of monomer use. RAFT mediated polymerization using RAFT agent 4,2-ethoxythiocarbonylsulfanyl-2-methyl-propionic acid (ETSPA) was found to provide a fairly narrow molecular weight distribution of the co-polymer product with the average Mw of the compositions being somewhat similar at the different MAHMP:NVP conditions. Based on these results it appeared that a MAHMP:NVP ratio of between 1:10 and 1:15 provided the best overall MAHMP content (10-15%) while retaining product yields of approximately 80% and with PDI of around 1.4-2.0.

| | Reactants equivalents | | | | MAHMP Mol % | Resultant MAHMP-Pyrrolidone Co-polymer |
|---|---|---|---|---|---|---|
| Batch no | A:B [A + B] | F | C | D | Incorp (H-NMR) | Yield, Molecular weight, PDI |
| IS09865-042 | 1:20 [50] | 1 | 6 | 3 | 4.6 | Yield: 88%, Mw: 3656 PDI: 1.74 |
| IS09865-093 | 1:15 [50] | 1 | 6 | 3 | 9.5 | Yield: 80%, Mw: 4799, PDI: 1.9 |
| IS09865-044 | 1:10 [50] | 1 | 6 | 3 | 15.2 | Yield: 78%, Mw: 3620, PDI: 1.60 |
| IS09865-041 | 1:5 [50] | 1 | 6 | 3 | 25.6 | Yield: 55%, Mw: 2298, PDI: 1.36 |

D. Repeatability Under Optimized Conditions

A series of polymerization tests to test repeatability of co-polymerization of MAHMP-NVP to form metal chelating compositions was performed in duplicate for the two MAHMP:NVP ratios of 1:15 and 1:10 as performed for example C above with results as shown in the table below.

| | Reactants equivalents | | | | MAHMP Mol % | Resultant MAHMP-Pyrrolidone Co-polymer |
|---|---|---|---|---|---|---|
| Batch no | A:B [A + B] | F | C | D | Incorp (H-NMR) | Yield and Molecular weight and PDI |
| IS09732-094 | 1:15 [50] | 1 | 6 | 3 | 9.9 | Yield: 92%, Mw: 3773 PDI: 1.8 |
| IS09732-096 | 1:15 [50] | 1 | 6 | 3 | 9.6 | Yield: 88%, Mw: 3792, PDI: 1.5 |
| IS09732-095 | 1:10 [50] | 1 | 6 | 3 | 15.3 | Yield: 85%, Mw: 3430, PDI: 1.6 |
| IS09732-097 | 1:10 [50] | 1 | 6 | 3 | 14.2 | Yield: 83%, Mw: 3602, PDI: 1.5 |

These results confirmed those for example C above and showed that a MAHMP:NVP ratio of between 1:10 to 1:15 provided high co-polymer product yields of >80%, product co-polymer Mw above 3 kDa with a low PDI (1.5 to 1.8) and an MAHMP content of the co-polymer product of 9.6-15.3% (w/w).

Example 13: Comparative True Molecular Weight and Molecular Weight Distribution of FRP and RAFT Prepared Co-Polymers Examination of the co-polymer as in example 7 was performed by Gel Permeation Chromatography (GPC) with molecular weight (both Mn (molecular weight number average and Mw, average molecular) and molecular distribution (PDI as Mw/Mn) inferred by reference to standards of known molecular weight. On this basis such Mw's would only be relative assessments and therefore not true Mw values. GPC analyses were performed on various co-polymer product samples as obtained with examples 3, 8, 11 and 12 using a Malvern GPC apparatus fitted with four discrete detectors to simultaneously measure separated eluted material for its viscosity, refractive index, ultra-violet light absorption and low angle laser light scattering. Refractive index and viscosity are both detectors for relative mass of material as separated by GPC while ultra violet absorption would detect relative MAHMP content of the separated materials. Laser light scattering (LS) allows measurement of the absolute molecular weight of the co-polymer. Absolute MW of the copolymer samples was measured according to Rayleigh theory on static light scattering which states that the intensity of light scattered (RΘ) at angle Θ is proportional to MW. The relationship between LS and MW is described by the Zimm equation where the optical constant, K, is dependent on (dn/dc)2 and is related to the intensity of scattered light (RΘ).

$$\frac{K \cdot c}{R_\theta} = \frac{1}{M_w P(\theta)} + 2A_2 c + 3A_3 c^2 + \ldots \quad \text{Zimm Equation}$$

$$K = \left(\frac{4\pi^2 n^2}{\lambda^4 N_A}\right)\left(\frac{dn}{dc}\right)^2 \quad \text{Optical Constant Equation}$$

Where $K$ = optical constant,
$c$ = concentration,
$R_\theta$ = Rayleigh scattering factor
(light scattering intensity),
$M_w$ = molecular weight,
$P(\theta)$ = particle scattering factor,
$A_i$ = viral coefficients,
$n$ = refractive index,
$\lambda$ = vacuum wavelength
of incident laser beam,
$N_A$ = Avagrado's Number (mol$^1$), and
$dn/dc$ = refractive index increment.

For absolute MW determination of the copolymers, the GPC system OmniSEC software generated an actual dn/dc value based on the respective dn/dc values of the monomers. The RI detector allowed measurement of the dn/dc values for calibration materials including homo-polymer PVP and MAHMP monomer providing a dn/dc value of 0.1218±0.0005 mL/g for PVP and 0.1958±0.0016 mL/g for MAHMP. A dn/dc value of 0.1420 mL/g for homo-polyacrylamide in 0.2 M NaNO$_3$ solution was obtained from American Polymer Standards Corporation. Compositional analysis of MAHMP content in the copolymers was carried out by measuring the ultra-violet (UV) absorbance at 280 nm. Polyacrylamide homopolymer had no detectable UV absorbance at 280 nm and the PVP homo-polymers had negligible UV absorbance with a relative dA/dc value of 4.76% compared to the Bovine Serum Albumin protein calibration standard. MAHMP had a very strong absorbance of UV with a very high relative dA/dc value compared to that obtained for the BSA standard.

Figure 11A:
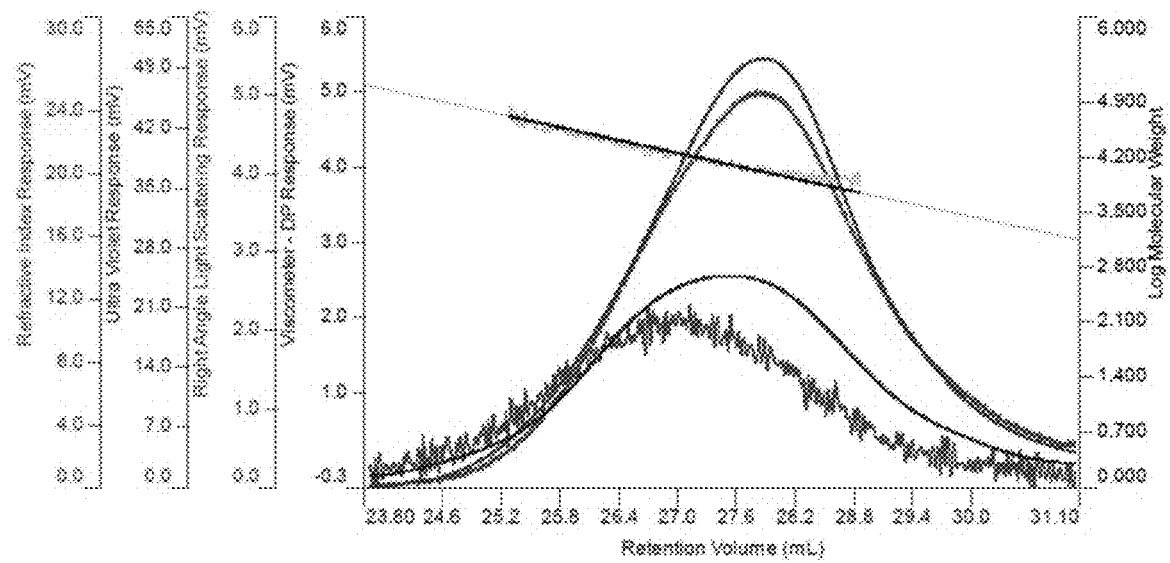
FIG. 11 shows a comparison of the molecular weight distributions of chelating compositions comprised of 3-hydroxy-1-(β-methacrylamidoethyl)-2-methyl-4(1H)-pyridinone (MAHMP) and 1-vinyl-2-pyrrolidone as prepared by FRP (FIG. 11A) and RAFT (FIG. 11B) polymerization procedures as characterized by the procedures shown in Example 13.
Figure 11B:
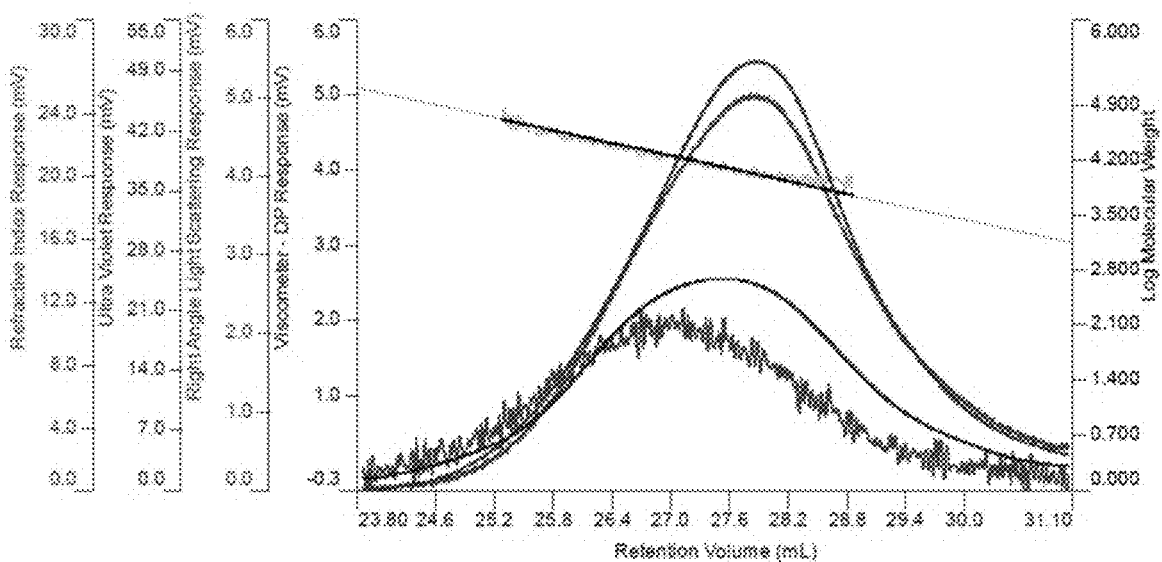
Figure 12A:
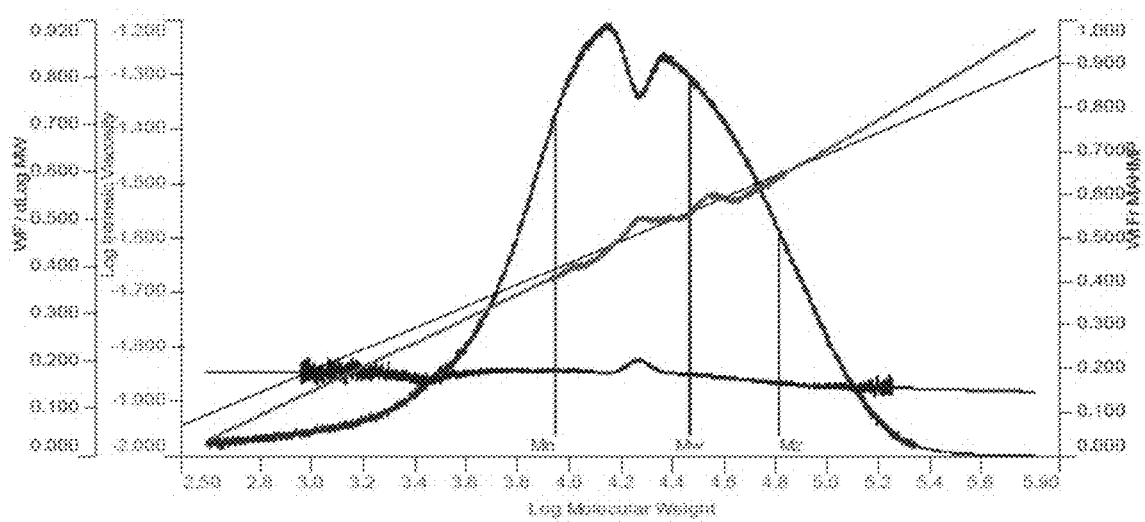
FIG. 12 shows a comparison of the molecular weight distributions of chelating compositions comprised of 3-hydroxy-1-(β-methacrylamidoethyl)-2-methyl-4(1H)-pyridinone (MAHMP) and 1-vinyl-2-pyrrolidone as prepared by FRP (FIG. 12A) and RAFT (FIG. 12B) polymerization procedures as characterized by the procedures shown in Example 13.
Figure 12B:
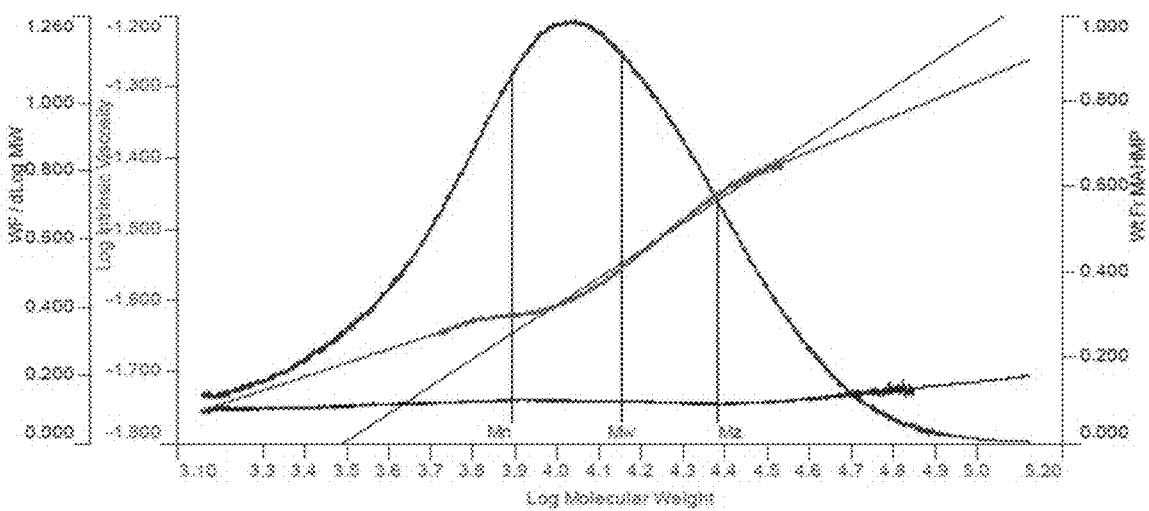
Figure 13A:
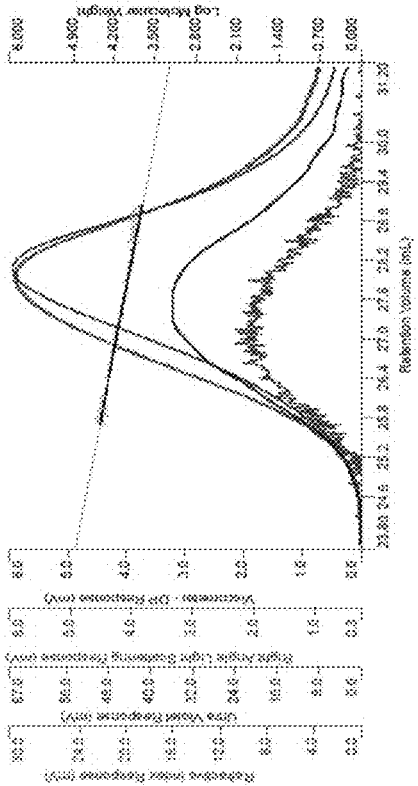
FIG. 13 shows a comparison of the molecular weight distributions of chelating compositions comprised of 3-hydroxy-1-(β-methacrylamidoethyl)-2-methyl-4(1H)-pyridinone (MAHMP) with N,N-dimethyl-acrylamide (FIGS. 13A and 13C) or 1-vinyl-2-pyrrolidone (FIGS. 13B and 13D) as prepared by RAFT polymerization procedures as characterized by the procedures described in Example 13.

The analyses of the GPC separated co-polymer compositions by these detectors provided useful information on the size distribution and chemical composition of these co-polymer compositions. FIG. 11 (A) shows the elution profile with detector responses for FRP prepared MAHMP-NVP co-polymer obtained as from Example 4B and the RAFT prepared MAHMP-NVP co-polymer (11B) obtained as from Example 12A. The broader distribution of molecular weight and higher average Mw for the FRP processed MAHMP-pyrrolidone copolymer sample as prepared in Example 4B (FIG. 11A) can be appreciated by comparison to the FRP processed composition as prepared in Example 12A (FIG. 11B). The FRP processed co-polymer appeared to have two broad peaks of co-polymer material of differing Mw's as shown in FIG. 12A for the FRP processed MAHMP-pyrrolidone copolymer sample as prepared in Example 4B. This was in contrast to the distribution shown in FIG. 12B for the RAFT prepared MAHMP-NVP co-polymer as obtained from Example 12A. Examination of the intrinsic viscosity relative to molecular weight revealed viscosity increased with increasing molecular weight. MAHMP content as measured by ultra-violet light absorption showed a relatively uniform MAHMP content across the molecular weight distribution for both FRP and RAFT prepared co-polymers. These results suggested that the MAHMP-pyrrolidone co-polymer was a random co-polymer of these two monomer units and that the MAHMP content was uniformly distributed across the co-polymer molecular weight distributions for both FRP and RAFT prepared co-polymers. Similar findings were obtained for other copolymers comprised of MAHMP with either pyrrolidone or acrylamide as shown for two additional samples in FIG. 13. A sample of MAHMP-acrylamide co-polymer (sample FS9758-037) as obtained in example 11C with the MAHMP addition done in two portions of MAHMP/DMA solution was found to have an average Mw of 76.4 kDa with a relatively narrow distribution of molecular weights of the co-polymer chains as shown in FIG. 13A. The MAHMP content of this sample was also distributed uniformly, i.e., randomly, across the size range of the co-polymer molecules as shown in FIG. 13C. Such a metal chelating co-polymer of relatively high molecular weight and with its corresponding higher viscosity as also shown in FIG. 13C may be more suitable than lower molecular weight compositions for application to mucosal or other surfaces of the body, i.e., where the physical properties of the metal chelating co-polymer such as bulkiness and higher viscosity would act to increase its physical retention time at the site of application.

Figure 13B:
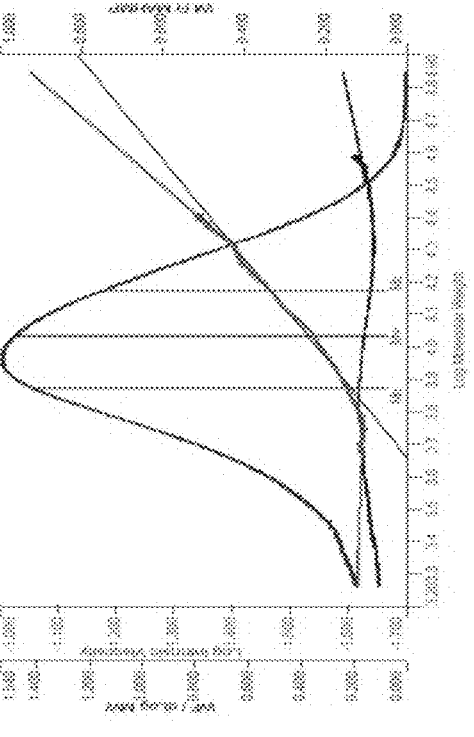
Figure 13C:
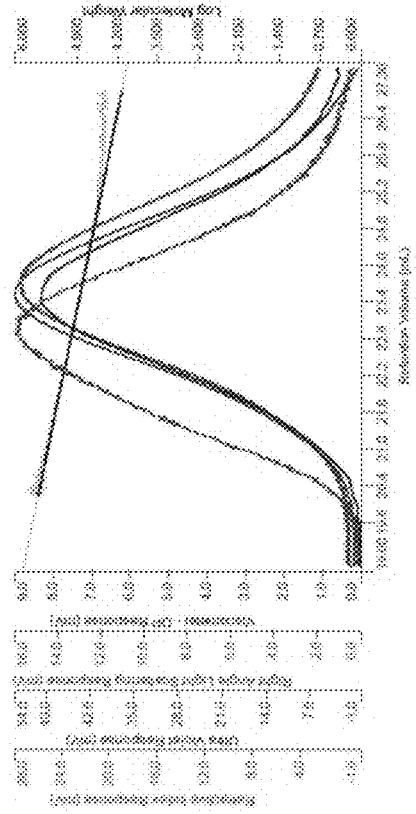
Figure 13D:
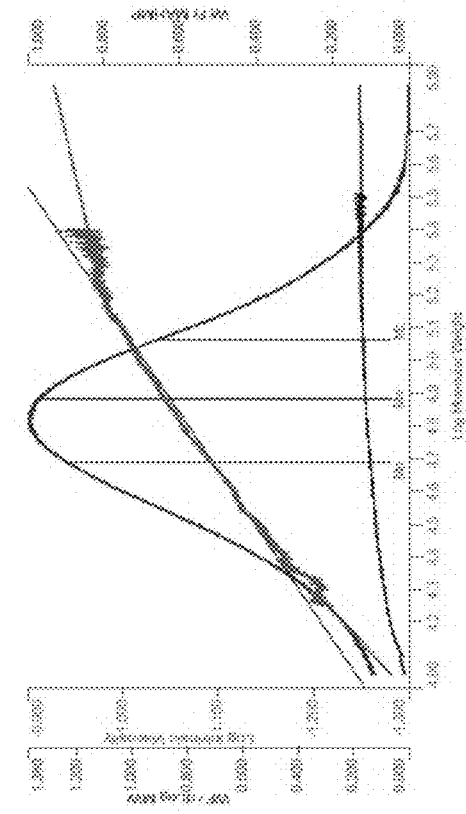

The reproducibility of the synthesis of MAHMP copolymers is also evident when an additional sample of a RAFT prepared MAHMP-pyrrolidone co-polymer composition (FS10912-058) prepared by the same method of Example 12A was analyzed as shown in FIG. 13B and FIG. 13D. The molecular weight distribution, viscosity profile and uniformity of MAHMP content across the size range of co-polymer molecules for this sample was similar to the characteristics of the similarly prepared sample as shown in FIG. 11B and FIG. 12B.

The true molecular weights of the metal chelating co-polymer compositions as determined by laser light scattering were found to be substantially higher as summarized in the table below than had been indicated by relative molecular weight determinations as determined with the methods of Example 7. PDI values were similar for both GPC methods indicating similar size separation of the samples by the two GPC column systems. However, true Mw's were on average 4.5× larger for RAFT prepared co-polymers than had been estimated using relative (to calibration standards) Mw determinations. There was a reasonable level of agreement in MAHMP contents as determined by $^1$H NMR spectroscopy as in Example 3 and by ultra-violet absorption measurements as above but not in all cases as seen in the table below

| Metal Chelating Composition | Relative Mw PDI (Conventional GPC) | True Mw PDI Laser-detector GPC | MAHMP Mol % ($^1$H NMR) | MAHMP % wt (UV abs) |
|---|---|---|---|---|
| RAFT prepared MAHMP-pyrrolidone copolymer Sample FS10912-061 ex example 12A | 2.4 kDa PDI = 1.8 | 13.3 kDa PDI = 1.8 | 12.6 | 9.8 |

| Metal Chelating Composition | Relative Mw PDI (Conventional GPC) | True Mw PDI Laser-detector GPC | MAHMP Mol % ($^1$H NMR) | MAHMP % wt (UV abs) |
|---|---|---|---|---|
| RAFT prepared MAHMP-pyrrolidone copolymer Sample FS10912-058 ex example 12A | 2.5 kDa PDI = 1.5 | 11.0 kDa PDI = 1.4 | 13.2 | 10.1 |
| FRP prepared MAHMP-pyrrolidone copolymer Sample P315-A00279-29 ex example 4B | 4.6 kDa PDI = 3.6 | 29.3 kDa PDI = 3.7 | 21.4 | 18.6 |
| FRP prepared MAHMP-pyrrolidone copolymer Sample ISO9758-045 ex example 4C | 4.7 kDa PDI = 2.4 | 32 kDa PDI = 2.4 | 14.5 | 8.8 |
| RAFT prepared MAHMP-acrylamide copolymer Sample FS9758-037 ex example 11A | 21.5 kDa PDI = 1.9 | 76.4 kDa PDI = 1.6 | 6.5 | 10.3 |

Example 14: Removal of RAFT Agent from Metal Binding Composition

Figure 14:
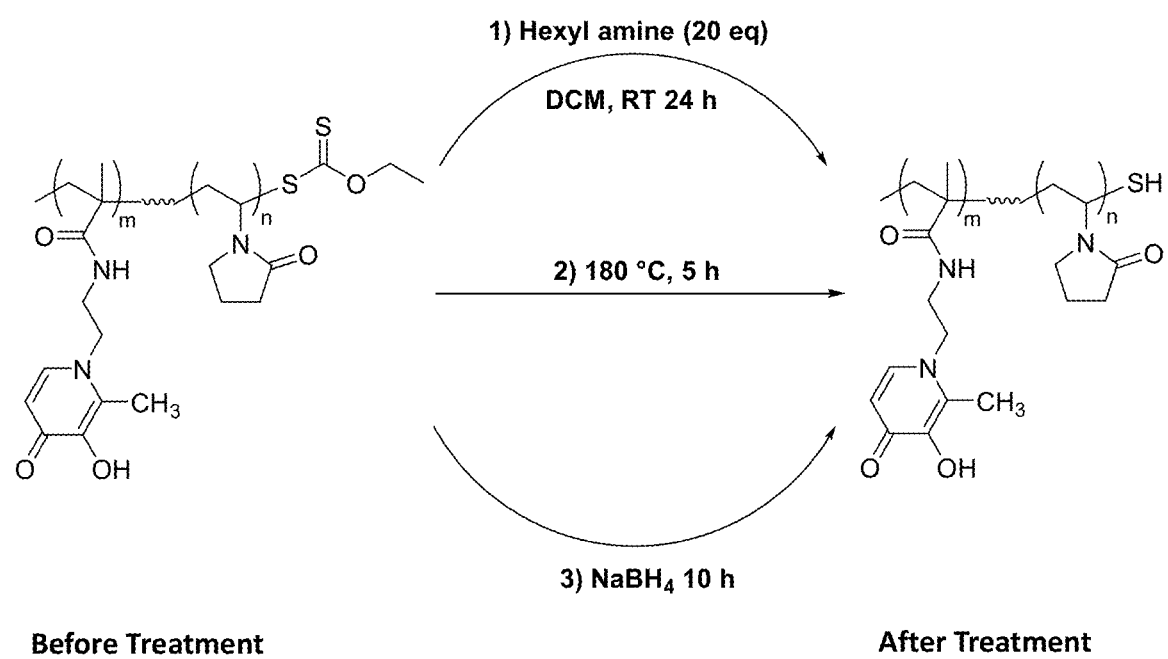
FIG. 14 shows exemplary procedures used to remove a portion of the RAFT agent from a chelating composition as made by RAFT mediated mechanisms with use of a RAFT agent as described in Example 14.

Removal of a portion or the entire RAFT agent that is present on one terminal of a metal chelating polymer chain prepared by the RAFT process may be desirable so as to reduce the sulfur content in the polymer. Partial removal of the RAFT agent from the chelating polymer compositions as prepared in Example 12 was tested using three separate methods, i.e., by aminolysis, by thermal treatment, and by the mild reducing agent, sodium borohydride as shown in FIG. 14.

Thermolysis of a sample of chelating polymer composition (9732-075) was first subjected to thermal treatment at 150° C. but there was no loss of sulfur content as measured by thermo-gravimetric analysis and elemental analysis showed no loss of sulfur content. Thereafter thermolysis was carried out at 180° C. and after five hours of heating there was a reduction in sulfur content from 0.53% (w/w) to 0.16% (w/w). This thermal treatment reduced the sulfur content by approximately 50% consistent with the reaction scheme and product shown in FIG. 16 (2). Aminolysis was also tested as an alternative to heat treatment. Chelating composition (9865-040 or 9865-044) was treated with hexyl-amine in dichloromethane for 24 h at room temperature and thereafter the treated composition was recovered an analyzed for its MAHMP content using the method of example 3, as well as its contents of elemental C, H, N and S in comparison to a sample of untreated composition as shown in the table below. The samples were also tested for their biological activities by determining their MIC values against *S. aureus* using the method of Example 6. The results in the table below show a removal of sulfur from the chelating composition following aminolysis treatment in that sulfur content dropped from 0.5% to 0.4%. There was no loss of MAHMP content or biological activity from aminolysis treatment of the composition. The aminolysis treatment removed approximately 20% of the sulfur content of the composition while complete formation of the treated structure shown in FIG. 14 might be expected to show a loss of 50% of the initial sulfur content.

| Sample | MAHMP % | MIC µg/mL | C % | H % | N % | S % |
|---|---|---|---|---|---|---|
| Before aminolysis | 15 | 4 | 57.5 | 7.7 | 11.2 | 0.5 |
| After aminolysis | 15 | 4 | 57.7 | 8.0 | 10.8 | 0.4 |

An alternate method for the removal of RAFT agent was tested using a modification of the procedure of Zelikin et al. (Zelikin, A. N.; Such, G. K.; Postma, A.; Caruso, F.; "Poly (vinylpyrrolidone) for Bioconjugation and Surface Ligand Immobilization." *Biomacromolecules*, 2007, 8, 2950-2953.). The co-polymer sample (0.2 mg) was dissolved in deionized water (16 mL), where the solution was then saturated with $N_2$ gas via a needle for 10 min. To this solution sodium borohydride (2 N, 4 mL) was added dropwise at room temperature, whereby vigorous bubbling occurred. The resultant mixture was left to stir at room temperature overnight. The excess amount of sodium borohydride was reacted with concentrated hydrochloric acid and the pH of solution was adjusted to 8 using 2 N sodium hydroxide. Water was then removed in vacuo yielding a beige film. The film was then re-dissolved in deionized water (16 mL) and dialyzed against water for two days with a membrane having a 3.5 kDa pore size.

Example 15: Activities of Metal Chelating Co-Polymers for Microbial Cells are Related to the Amount of Metal Binding Monomer Incorporated into the Structure Chelating compositions prepared as in Example 12C with different amounts of MAHMP incorporated into the polymer structure were tested for their activities for inhibition of the growth of *Staphylococcus aureus* using the method described in as in Example 6. The results shown in the table below show a direct relationship of the amount of MAHMP incorporated into the polymer chelating composition to the chelating composition's activity against the bacterium. The three compositions shown had somewhat similar relative molecular weights of around 2-4 kDa and a relatively low PDI as measured by relative conventional GPC as described in Example 7. Activity of the compositions for inhibiting growth the bacterial cells was also compared to MAHMP alone, i.e. MAHMP free and not incorporated into a chelating composition. This example also demonstrates the relatively high activity (low MIC for bacteria) of the chelating compositions and the relatively low activity (correspondingly high MIC) for the free MAHMP iron-binding molecule when it is not incorporated as part of the structure of the chelating composition. The chelating compositions were all above 1500 Da molecular weight and had activity for the bacterial cells causing inhibition of growth.

| Composition Batch No. | Synthesis Method | MAHMP Mol % in composition | Composition Molecular Weight Mw and (PDI) | MIC for *S. aureus* µg/mL |
|---|---|---|---|---|
| 9732-093 | RAFT-4 NVP:MAHMP 15:1 | 9.54 | 4.8 kDa (1.9) | 8 |
| 9732-095 | RAFT-4 NVP:MAHMP 10:1 | 15.3 | 3.4 kDa (1.6) | 4 |
| 9865-041 | RAFT-4 NVP:MAHMP 5:1 | 25.6 | 2.3 kDa (1.9) | 2 |

| Composition Batch No. | Synthesis Method | MAHMP Mol % in composition | Composition Molecular Weight Mw and (PDI) | MIC for S. aureus µg/mL |
|---|---|---|---|---|
| NA | MAHMP alone not incorporated into composition | 100% MAHMP not in composition | 236 Da (1.0) | 125 |

Figure 15A:
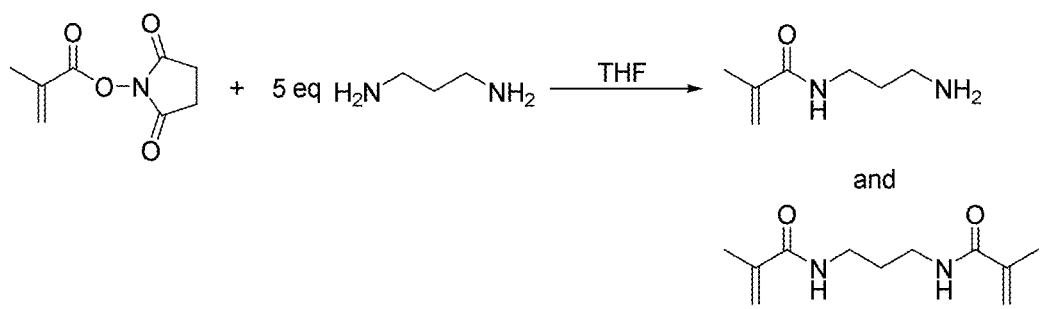
FIG. 15A shows exemplary procedures for the synthesis of N-(3-aminopropyl)methacrylamide.

Example 16: Preparation of 3-Hydroxy-1-(β-Methacrylamido-R)-2-Methyl-4(11)-Pyridinone Compounds with R Comprising a Carbon Chain of >2 and ≤12 Carbon Units A. Synthesis of N-(3-aminopropyl)methacrylamide (FIG. 15A)

N-hydroxysuccinimide methacrylate (100 mg, 0.5 mmol) was added to a 25 mL Schlenk tube under nitrogen atmosphere. To this 10 mL of anhydrous THF was added with stirring. The resultant mixture was cooled to 0° C. To the cooled mixture, 1,3-propanediamine (0.28 mL, 2.7 mmol) was added with a syringe, whereupon a white precipitate immediately formed. The reaction mixture was warmed to room temperature and stirred overnight. The following day, the white precipitate was filtered off by gravity filtration and washed with THF (3×10 mL). The filtrate and THF washings are collected and the solvent was removed under reduced pressure to yield and clear oil. $^1$H NMR spectrum in $d_6$-DMSO of the crude oil identified a mixture of 1,3-propanediamine, N,N'-1,3-propanediylbis(2-methyl-2-propenamide), and N-(3-aminopropyl)methacrylamide. According to the $^1$H NMR spectrum, N-(3-aminopropyl)methacrylamide was 90% respective to N,N'-1,3-propanediylbis(2-methyl-2-propenamide). $^1$H NMR (400 MHz, $d_6$-DMSO): δ 8.00 (bs, 1H) 5.62 (s, 1H), 5.30 (s, 1H), 3.15 (q, 2H), 1.85 (s, 3H), 1.49 (pent, 2H), 1.43-1.16* (m, 2H).
*Signal overlapping with 1,3-propanediamine signals.

Figure 15B:
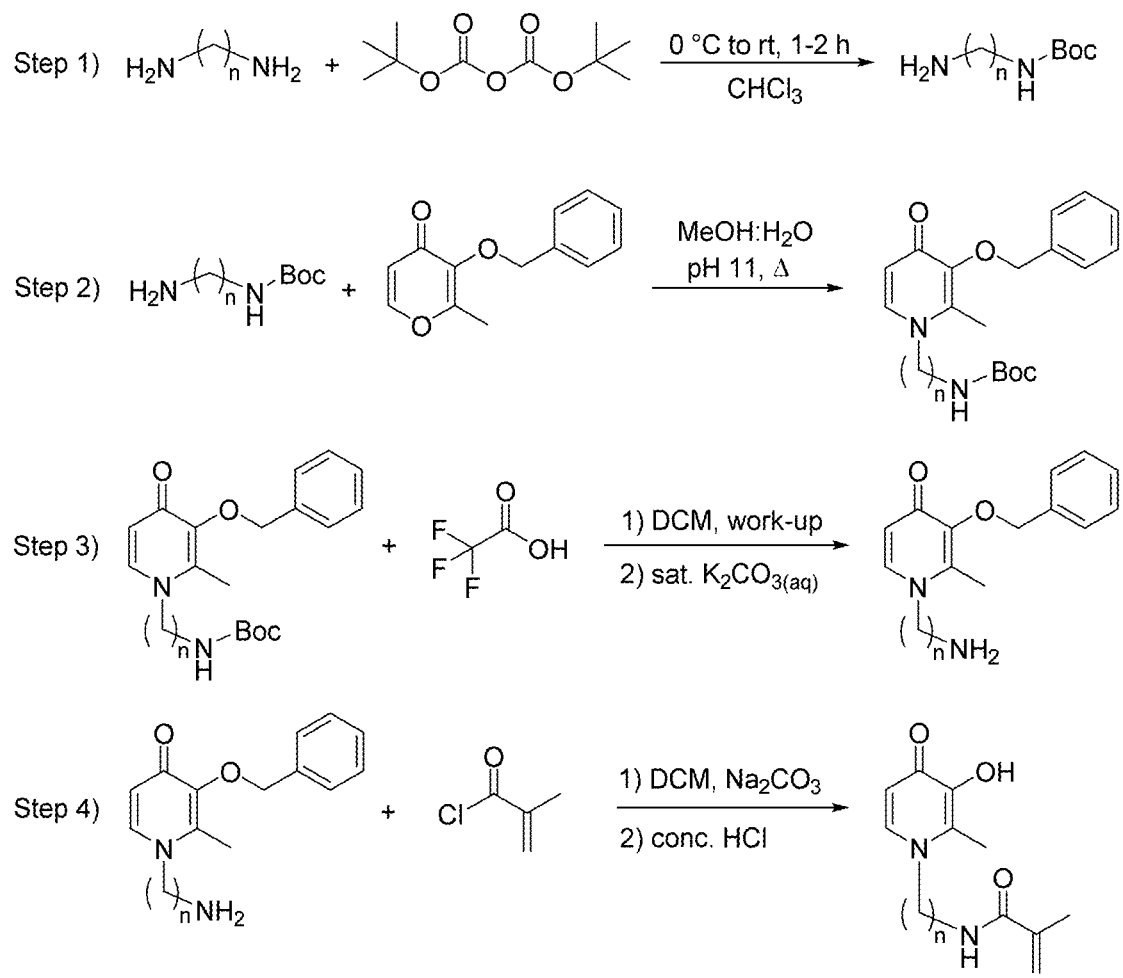
FIGS. 15B and 15C show general schemes for the formation of 3-hydroxy-1-(β-methacrylamido-R)-2-methyl-4 (1H)-pyridinones as described in Example 16.

The tert-Butyloxycarbonyl protecting group (Boc) can be used for the protection of an amine group of an alkanediyl diamine towards the synthesis 3-hydroxy-1-(β-methacrylamido-R)-methyl-4(1H)-pyridinones with the general procedure shown in FIG. 15B. A representative example is described below starting by the Boc-protection of 1,8-diaminooctane (adopted procedure from Maris Cinelli et al. Bioorg. Med. Chem., 2009, 17(20), 7145-7155).

B. Synthesis of 3-hydroxy-1-(β-methacrylamidooctyl)-2-methyl-4(1H)-pyridinone (General Procedure Illustrated in FIG. 15B)

Di-tert-butyl dicarbonate (1.9 g, 8.7 mmol in 40 mL of CHCl$_3$) was added dropwise over 1 h to a solution of 1,8-diaminooctane (6.3 g mL, 44 mmol) in CHCl$_3$ (200 mL) at room temperature and stirred overnight. The solution was then diluted with CHCl$_3$ (100 mL) and washed with saturated K$_2$CO$_3$ (2×50 mL) followed by H$_2$O (2×50 mL). The organic layer was separated, dried over MgSO$_4$, and concentrated in vacuo. The crude viscous solution was then adsorbed onto SiO$_2$ and purified by column chromatography eluting with 10% MeOH/1% NEt$_3$ in CHCl$_3$ to yield the Boc-protected 1,8-diaminooctane as a clear colourless oil (1.9 g) in 90% yield (Step 1 of FIG. 15B). $^1$H NMR (400 MHz, $d_6$-DMSO): δ 3.35 (bs, 1H), 2.88 (q, 2H), 2.49 (t, 2H), 1.37 (s, 9H), 1.35-1.28 (m, 4H), 1.27-1.13 (m, 8H). The Boc-protected 1,8-diaminooctane (1.9 g) was dissolved in MeOH:H$_2$O (1.5:1 50 mL). The resultant solution was added to a stirring solution of 3-benzyloxy-2-methyl-4-pyrone (1.68 g, 7.8 mmol) in MeOH:H$_2$O (1.5:1, 50 mL). After stirring for 5 min, the reaction mixture was charged with a 2 N NaOH solution (10 mL). The final solution was heated at 90° C. for 2 h. The reaction mixture was cooled to room temperature and the solvent was removed under reduced pressure. The oily residue obtained was then diluted with water (50 mL) and the pH was maintained at 7.0 with 2 N HCl. The aqueous layer was then extracted with methylene chloride (3×25 mL). The organic layers were then collected and dried with Na$_2$SO$_4$ and then concentrated under reduced pressure to yield brown colored oil (2.9 g) in 85% yield. $^1$H NMR spectroscopy confirmed the structure of N-Boc-(2-(3-(benzyloxy)-2-methyl-4-oxopyridin-1(4H)-yl)octyl)-carbamate (Step 2 of FIG. 15B). $^1$H NMR (400 MHz, $d_6$-DMSO): δ 7.40 (d, 1H), 7.38-7.29 (m, 5H), 6.77 (bs, 1H), 6.13 (d, 1H), 5.02 (s, 2H), 3.84 (t, 2H), 2.88 (q, 2H), 2.14 (s, 3H), 1.57-1.52 (m, 2H), 1.36 (s, 9H), 1.23-1.21 (m, 10H). $^{13}$C NMR (100 MHz, DMSO-$d_6$): δ 172.2, 156.0, 145.6, 141.0, 139.9, 138.2, 128.9, 128.8, 128.6, 128.3, 128.1, 116.4, 77.7, 72.1, 53.1, 39.3, 30.5, 29.9, 29.0, 28.7, 26.7, 26.1, 12.3. Removal of the Boc-group was achieved by dissolving the oil in 30 mL of dichloromethane with an excess amount of TFA (4 mL) and stirring the solution overnight at room temperature. The following day 4 mL of 2 N NaOH was added to react with any residual amount of TFA. 20 mL of dichloromethane was added to the crude solution and extracted with 3×20 mL of water. The aqueous layers were collected and reduced to half the volume. A saturated solution of potassium carbonate (40 mL) was added to the solution of the TFA-salt and stirred at room temperature overnight. The aqueous phase was then extracted with dichloromethane (3×25 mL). The organic layers were then collected and dried with Na$_2$SO$_4$ and then concentrated under reduced pressure to yield 1-aminooctyl-3-hydroxy-2-methyl-4(1H)-pyridinone as a brown colored oil (1.1 g) in 49% yield (Step 3 of FIG. 15B). $^1$H NMR (400 MHz, $d_6$-DMSO): δ 7.60 (d, 1H), 7.46-7.25 (m, 5H), 6.14 (d, 1H), 5.02 (s, 2H), 3.84 (t, 2H), 2.6-2.48 (m, 2H), 2.14 (s, 3H), 1.63-1.44 (m, 2H), 1.41-1.01 (m, 10H) (Step 3 of FIG. 15B). The oil was then dissolved in 30 mL of dichloromethane under a nitrogen atmosphere where Na$_2$CO$_3$ (1.6 g) was added to the solution and the resultant mixture was stirred at room temperature for 30 min. The solution was cooled to 0° C. and following 10 min, methacryloyl chloride (0.3 mL) was added dropwise over 10 min. The resultant solution was left to warm to room temperature and stirred for 1 h. The reaction mixture was then poured over a 1.5:1 solution of dichloromethane and water. The solution was extracted with 1 N HCl (2×10 mL) and water (2×10 mL). The organic layers were collected and dried with Na$_2$SO$_4$ and the solvent was removed under reduced pressure. The crude product (0.9 g) was used without further purification and 37% wt. HCl (8 mL) was added to the residue and the resultant solution was stirred overnight at room temperature. The following day, the acidic water layer was removed under reduced pressure and the isolated brown colored oil was dissolved in 10 mL of water and 10% NaHCO$_3$ solution was added to reach a pH of 7. The aqueous layer was then extracted with dichloromethane (3×10 mL) and the organic layers were collected and dried with Na$_2$SO$_4$. Removal of the solvent revealed 3-hydroxy-1-(β-methacrylamidooctyl)-2-methyl-4(1H)-pyridinone as a brown oil (0.56 g) in 82% yield (Step 4 of FIG. 15B). $^1$H NMR (400 MHz, d$_6$-DMSO): δ 7.89 (bs, 1H), 7.59 (d, 1H), 7.13 (d, 1H), 5.63-5.59 (m, 1H), 5.32-5.27 (m, 1H), 3.92 (t, 2H), 3.08 (q, 2H), 2.28 (s, 3H), 1.84 (s, 3H), 1.69-1.52 (m, 2H), 1.49-1.34 (m, 2H), 1.32-1.16 (m, 10H). $^{13}$C NMR (100 MHz, DMSO-d$_6$): δ 168.7, 167.8, 145.8, 140.6, 138.1, 129.6, 119.1, 110.9, 53.4, 30.7, 29.5, 29.1, 28.9, 26.8, 26.2, 19.2, 11.8. ESI-MS [M+H]$^+$ calcd for C$_{18}$H$_{29}$N$_2$O$_3$: 321.22, found 321.23.

Figure 15C:
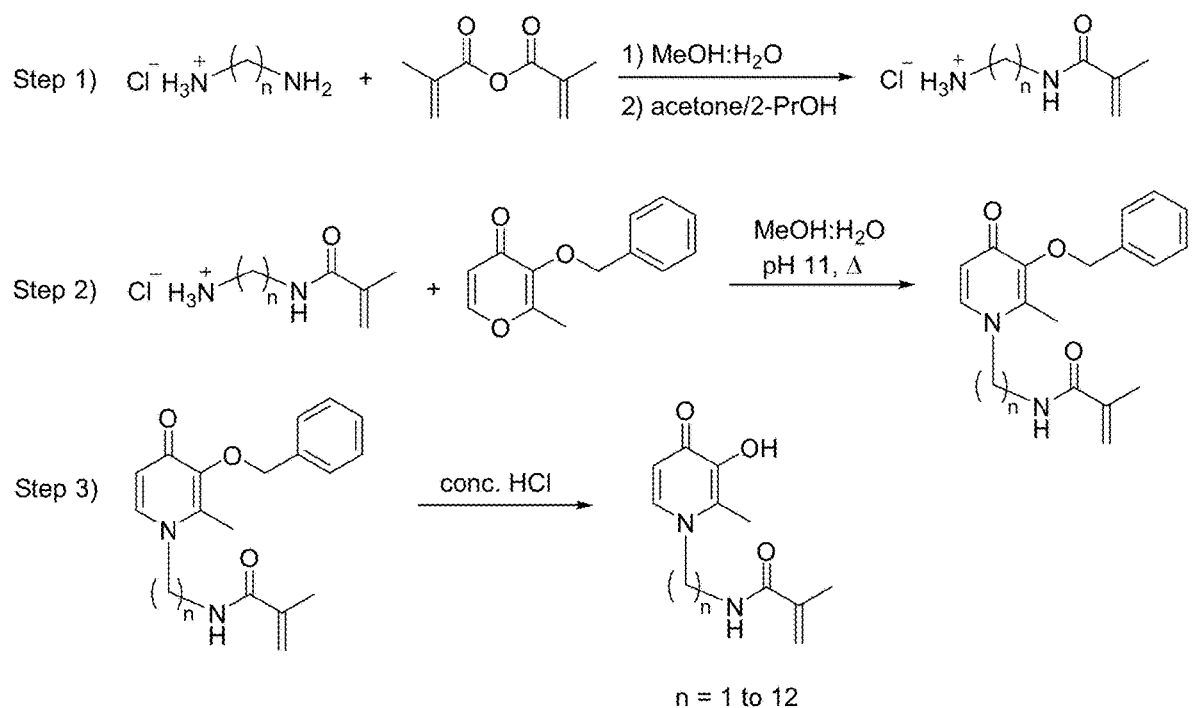

Structure b.HCl (FIG. 2B, Path B) was produced using methacrylic anhydride and ethylenediamine. The same method was adapted using longer chain alkanediyl diamines to produce the corresponding N-(2-amino-R-)methacrylamides (General procedure in FIG. 15C) towards the corresponding 3-hydroxy-1-(β-methacrylamido-R)-2-methyl-4 (1H)-pyridinones. A representative example is illustrated below for the synthesis of 3-hydroxy-1-(β-methacrylamidobutyl)-2-methyl-4(1H)-pyridinone.

C. Synthesis of 3-hydroxy-1-(β-methacrylamidobutyl)-2-methyl-4(1H)-pyridinone (General Procedure in FIG. 15C)

1,4-diaminobutane (5.0 g, 57 mmol, 2.0 equiv) was added to a solution of 1,4-diaminobutane dihydrochloride (4.6 g, 28 mmol, 1.0 equiv) in 50 mL of water. After 1.5 h of stirring at room temperature, methanol (55 mL) was added and the mixture was cooled to 0° C. allowing the temperature to equilibrate for 15 min. Methacrylic anhydride (12.6 mL, 85 mmol, 3.0 equiv) dissolved in methanol (15 mL) was added dropwise over 15 min to the cooled solution. After complete addition of the methacrylic anhydride, the solution temperature was maintained at 0° C. for 1 h. 37% wt. Hydrochloric acid (10 mL) was added to the cooled solution and continued for 1 h and the solution was allowed to warm up to room temperature. The solvent was removed under reduced pressure to yield a crude viscous mass that was then delivered slowly into acetone (400 mL). The precipitate was isolated and collected by vacuum filtration followed by extraction with hot 2-propanol (150 mL). The 2-propanol extracts were concentrated under reduced pressure and a minimal amount of acetone was used to precipitate the product. It was then isolated and dried with vacuum filtration to give 6 g (48% yield) of the product as an off-white powder. $^1$H NMR (400 MHz, DMSO-d$_6$): δ 8.26-7.79 (m, 4H), 5.66 (bs, 1H), 5.31 (bs, 1H) 3.11 (q, 2H), 2.84-2.68 (m, 2H), 1.85 (s, 3H), 1.66-1.37 (m, 4H). $^{13}$C NMR (100 MHz, DMSO-d$_6$): δ 167.9, 140.5, 119.4, 38.9, 38.5, 26.5, 24.9, 19.2. N-(2-aminobutyl)methacrylamide dihydrochloride (5.5 g, 29 mmol) was dissolved in a solution of MeOH:H$_2$O (1.5:1, 75 mL) and added to a stirring solution of 3-(benzyloxy)-2-methyl-4H-pyran-4-one in MeOH:H$_2$O (1.5:1, 75 mL). The pH was adjusted to 10 with 28 mL of 2 N NaOH and the resultant solution was heated for 3 h at 85° C. The reaction was cooled and half the volume was removed under reduced pressure. 50 mL of water was added to the solution and then the solution pH was adjusted to 7 with 20 mL of 1 N HCl. The aqueous layer was then extracted with dichloromethane (3×30 mL). The organic layers were collected, dried with Na$_2$SO$_4$ and removed under reduced pressure. The crude viscous oil was then purified by column chromatography eluting with 10% MeOH/1% NEt$_3$ in CHCl$_3$ to isolate N-[2-(3-(benzyloxy)-2-methyl-4-oxopyridin-1(4H)-yl) butyl] methacrylamide as a brown oil (5.1 g) in 60% yield. $^1$H NMR (400 MHz, DMSO-d$_6$): δ 7.95 (t, 1H), 7.60 (d, 2H), 7.46-7.27 (m, 5H), 6.14 (d, 2H), 5.63 (bs, 1H), 5.31 (bs, 1H), 3.87 (t, 2H), 3.12 (q, 2H), 2.15 (s, 3H), 1.85 (s, 3H), 1.62-1.50 (m, 2H), 1.47-1.35 (m, 2H). $^{13}$C NMR (100 MHz, DMSO-d$_6$): δ 172.2, 167.9, 145.7, 141.0, 140.5, 141.0, 140.5, 139.9, 138.2, 128.9, 128.6, 128.3, 119.3, 116.4, 72.2, 52.9, 38.6, 28.0, 26.4, 19.2, 12.3. N-[2-(3-(benzyloxy)-2-methyl-4-oxopyridin-1(4H)-yl)butyl] methacrylamide (2.9 g) was treated with 21 mL of 37% wt. HCl and the resultant mixture was stirred overnight at room temperature. The aqueous layer was removed under reduced pressure producing a brown oily residue. To this 30 mL of water was added and the solution pH was adjusted to 7 using 20 mL of 10% NaHCO$_3$. Insoluble precipitates were removed from the aqueous layer by gravity filtration. The aqueous layer was then reduced to a minimal volume under reduced pressure and the product, 3-hydroxy-1-(β-methacrylamidobutyl)-2-methyl-4(1H)-pyridinone, precipitated from solution. The product was collected, washed with 5 mL of water, and dried by vacuum filtration. The light brown solid (1.1 g) was isolated in 52% yield. $^1$H NMR (400 MHz, DMSO-d$_6$): δ 8.03-7.89 (m, 1H), 7.57 (d, 1H), 6.11 (d, 1H), 5.62 (bs, 1H), 5.31 (bs, 1H), 3.93 (t, 2H), 3.13 (q, 2H), 2.28 (s, 3H), 1.84 (s, 3H), 1.68-1.54 (m, 2H), 1.50-1.37 (m, 2H). $^{13}$C NMR (100 MHz, DMSO-d$_6$): δ 169.3, 167.9, 146.0, 138.0, 128.9, 119.3, 110.9, 52.9, 38.6, 28.2, 26.4, 19.1, 11.8. ESI-MS [M+H]$^+$ calcd for C$_{14}$H$_{21}$N$_2$O$_3$: 265.16, found 265.1570.

E. NMR chemical shifts for N-(2-amino-R-)methacrylamides, N-[2-(3-(benzyloxy)-2-methyl-4-oxopyridin-1(4H)-yl)-R] methacrylamide 3-hydroxy-1-(β-methacrylamido-R)-2-methyl-4(1H)-pyridinones (R=propyl or hexyl)

R=propyl:

N-(2-aminopropyl)methacrylamide $^1$H NMR (400 MHz, DMSO-d$_6$): δ 8.37-8.20 (m, 1H), 8.20-7.98 (m, 3H), 5.68 (bs, 1H), 5.31 (bs, 1H), 3.16 (q, 2H), 2.81-2.67 (m, 2H), 1.83 (s, 3H), 1.79-1.69 (m, 2H). $^{13}$C{$^1$H} NMR (100 MHz, DMSO-d$_6$): δ 168.3, 140.0, 119.9, 37.1, 36.2, 27.5, 19.1.

N-[2-(3-(benzyloxy)-2-methyl-4-oxopyridin-1(4H)-yl)propyl] methacrylamide $^1$H NMR (400 MHz, DMSO-d$_6$): δ 7.99 (t, 1H), 7.63 (d, 1H), 7.45-7.28 (m, 5H), 6.15 (d, 1H), 5.65 (bs, 1H), 5.33 (bs, 1H), 5.02 (s, 2H), 3.88 (t, 2H), 3.13 (q, 2H), 2.15 (s, 3H), 1.86 (s, 3H), 1.83-1.72 (m, 2H). $^{13}$C{$^1$H} NMR (100 MHz, DMSO-d$_6$): δ 172.3, 168.2, 145.9, 140.9, 140.4, 139.9, 138.2, 128.9, 128.7, 128.3, 119.5, 116.5, 72.2, 51.1, 36.4, 30.5, 19.1, 12.2. ESI-MS [M+H]$^+$ calcd for C$_{20}$H$_{25}$N$_2$O$_3$: 341.19, found 341.1868.

3-hydroxy-1-(β-methacrylamidopropyl)-2-methyl-4 (1H)-pyridinone $^1$H NMR (400 MHz, DMSO-d$_6$): δ 8.19-8.10 (m, 1H), 7.64 (d, 1H), 6.11 (d, 1H), 5.68 (bs, 1H), 5.33 (bs, 1H), 3.95 (t, 2H), 3.15 (q, 2H), 2.27 (s, 3H), 1.86 (s, 3H), 1.85-1.75 (m, 2H). $^{13}$C {$^1$H} (100 MHz, DMSO-d$_6$) 169.3, 168.2, 146.0, 140.3, 138.1, 128.8, 119.6, 110.9, 51.2, 36.4, 30.6, 19.1, 11.7. ESI-MS [M+H]$^+$ calcd for C$_{13}$H$_{19}$N$_2$O$_3$: 251.14, found 251.1400.

R=hexyl:

N-(2-aminohexyl)methacrylamide $^1$H NMR (400 MHz, DMSO-d$_6$): δ 8.28-8.03 (m, 3H), 8.02-7.90 (m, 1H), 5.64 (bs, 1H), 5.29 (bs, 1H), 3.09 (q, 2H), 2.79-2.67 (m, 2H), 1.84 (s, 3H), 1.62-1.49 (m, 2H), 1.49-1.37 (m, 2H), 1.36-1.18 (m, 4H). $^{13}C\{^{1}H\}$ NMR (100 MHz, DMSO-$d_6$): δ 167.8, 140.5, 119.2, 39.1, 39.0, 29.3, 27.3, 26.4, 26.0.

N-[2-(3-(benzyloxy)-2-methyl-4-oxopyridin-1 (4H)-yl)hexyl] methacrylamide $^{1}H$ NMR (400 MHz, DMSO-$d_6$): δ 7.91 (t, 1H), 7.59 (d, 1H), 7.44-7.27 (m, 5H), 6.15 (d, 1H), 5.63 (bs, 1H), 5.29 (bs, 1H), 5.03 (s, 2H), 3.84 (t, 2H), 3.09 (q, 2H), 2.14 (s, 3H), 1.84 (s, 3H), 1.61-1.49 (m, 2H), 1.47-1.37 (m, 2H), 1.31-1.15 (m, 4H). $^{13}C\{^{1}H\}$ NMR (100 MHz, DMSO-$d_6$): δ 172.29, 167.85, 145.76, 141.1, 140.6, 139.9, 138.2, 128.9, 128.6, 128.3, 119.2, 116.4, 72.2, 53.2, 30.5, 29.4, 26.5, 19.2, 12.3.

3-hydroxy-1-(β-methacrylamidohexyl)-2-methyl-4 (1H)-pyridinone $^{1}H$ NMR (400 MHz, DMSO-$d_6$): δ 7.88 (m, 1H), 7.56 (d, 1H), 6.10 (d, 1H), 5.62 (bs, 1H), 5.30 (bs, 1H), 3.91 (t, 2H), 3.08 (q, 2H), 2.28 (s, 3H), 1.84 (s, 3H), 1.68-1.56 (m, 2H), 1.49-1.36 (m, 2H), 1.34-1.19 (m, 4H). $^{13}C\{^{1}H\}$ NMR (100 MHz, DMSO-$d_6$): δ 169.3, 167.8, 149.9, 140.6, 138.0, 128.8, 119.1, 110.9, 53.2, 30.7, 29.4, 26.5, 25.9, 19.2, 11.8. ESI-MS [M+H]$^+$ calcd for $C_{16}H_{25}N_2O_3$: 293.19, found 293.1869.

Example 17: Microbial Activity for the Co-polymers Formed from 3-hydroxy-1-(β-methacrylamidobutyl)-2-methyl-4(1H)-pyridinone and 3-hydroxy-1-(β-methacrylamidohexyl)-2-methyl-4(1H)-pyridinone A red color was detected for each congener in the presence of iron that indicated the retention of the metal-binding affinity for each congener. The compound I-related congeners, that stemmed from the butyl and hexyl alkanediyl diamines were co-polymerized with NVP by the optimized conditions described in Example 12A using a reaction temperature range 40-50° C. The Compound (I)-related co-polymers were tested, alongside a co-polymer containing Compound (II) (MAHMP) synthesized according to the optimized conditions (Example 12A), for their activities for inhibition of the growth of Staphylococcus aureus and Candida albicans by microdilution broth assay. The co-polymers of butyl and hexyl Compound (I)-related congeners (Entry 3 and 4) showed comparable activity to the Compound (II) co-polymer (Entry 2) in dimethyl sulfoxide (DMSO). This demonstrated that with the change in monomer chain length did not inhibit microbial activity.

| Entry | Chelating Composition | S. aureus ATCC43300 MIC μg/mL 24 h | S. aureus ATCC43300 MIC μg/mL 48 h | C. albicans SC5324 WT MIC μg/mL 24 h | C. albicans SC5324 WT MIC μg/mL 48 h (MIC 80%) |
|---|---|---|---|---|---|
| 1 | Compound (II) co-polymer in RPMI | 4 | 4 | 4 | 4.0-8 |
| 2 | Compound (II) co-polymer in DMSO | 2 | 2 | 1 | 1 |
| 3 | Butyl co-polymer in DMSO (Compound (I) wherein R$^1$ is H, R$^2$ is methyl, R$^3$ is methyl, n is 4) | 2 | 2 | 2 | 2 |
| 4 | Hexyl co-polymer in DMSO (Compound (I) wherein R$^1$ is H, R$^2$ is methyl, R$^3$ is methyl, n is 6) | 2 | 2 | 1 | 1 |

Various embodiments of chelating compositions, methods of preparation and uses have been described. The above-described embodiments are intended to be examples, and alterations and modifications may be effected thereto by those of ordinary skill in the art without departing from the spirit and scope of the teachings.

What is claimed is:
1. A chelating composition soluble in aqueous media with chelating activity for an essential metal, the chelating composition prepared from:
at least a first and a second monomer unit, wherein the first monomer unit comprises one or more suitable metal binding chemical groups incorporated or affixed thereto optionally independently selected from the group consisting of carboxyl, hydroxyl, phenolate, catecholate, hydroxamate, hydroxypyridinone and hydroxyphenyltriazole; wherein:
the first and second monomer units are polymerized by a reversible addition-fragmentation chain transfer mechanism with the use of a suitable addition-fragmentation chain transfer agent;
optionally, the first monomer unit is represented by Compound (I)

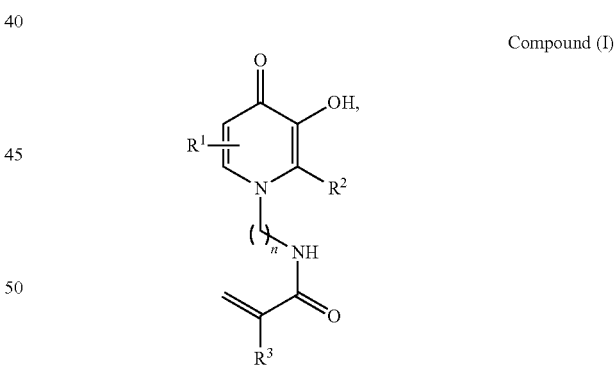

Compound (I)

wherein
R$^1$ is independently selected from the group consisting of H, alkyl and alkyl substituted with O, N or S;
R$^2$ is independently selected from the group consisting of H, alkyl and alkyl substituted with O, N or S;
R$^3$ is independently selected from the group consisting of H, alkyl and alkyl substituted with O, N or S; and
n is 1 to 12;
optionally the second monomer unit is independently selected from the group consisting of 1-vinyl-2-pyrrolidone, acrylic acid, methyl methacrylate, N,N-dimethyl-acrylamide, ethyl methacrylate, N-vinyl imidazole and styrene;

and
the resulting chelating composition binds one or more essential metal in an in vitro or in vivo environment of a living cell or organism and thereby affects the living cell or organism.

2. The chelating composition of claim 1, wherein the one or more suitable metal binding chemical groups are the hydroxypyridinone

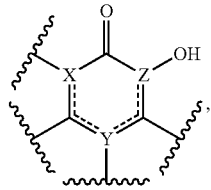

wherein X, Y and Z are independently N or C such that:
when X is N, Y and Z are C,
when Y is N, X and Z are C, and
when Z is N, X and Y are C.

3. The chelating composition of claim 1, wherein Compound (I) is prepared by polymerizing Compound (Ia)

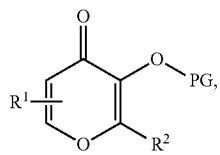

Compound (Ia)

wherein
$R^1$ is independently selected from the group consisting of H, alkyl and alkyl substituted with O, N or S;
$R^2$ is independently selected from the group consisting of H, alkyl and alkyl substituted with O, N or S; and
PG is a protecting group,
with Compound (Ib)

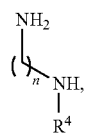

Compound (Ib)

wherein
n is 1 to 12; and
$R^4$ is $COCCH_2R^3$ or a protecting group,
followed by:
when $R^4$ is $COCCH_2R^3$, removing PG to yield Compound (I); or
when $R^4$ is a protecting group, removing $R^4$, reacting with a suitable acrylate source, and removing PG to yield Compound (I).

4. The chelating composition of claim 1, wherein
$R^1$ is H;
$R^2$ is methyl;
$R^3$ is methyl; and
n is 1 to 6 or optionally n is at least 2.

5. The chelating composition of claim 1, wherein the first monomer unit is
represented by Compound (II)

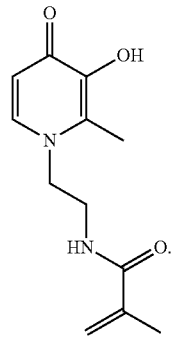

Compound (II)

6. The chelating composition of claim 1, wherein the second monomer unit is 1-vinyl-2-pyrrolidone.

7. The chelating composition of claim 1, wherein the second monomer unit is N,N-dimethyl-acrylamide.

8. The chelating composition of claim 1, wherein the suitable addition-fragmentation chain transfer agent is independently selected from the group consisting of 2-ethoxy-thiocarbonylsulfanyl-propionic acid ethyl ester and 2-ethoxythiocarbonylsulfanyl-2-methyl-propionic acid.

9. The chelating composition of claim 1, wherein a residue of the addition-fragmentation chain transfer agent is removed in whole or in part from the chelating composition after polymerization.

10. The chelating composition of claim 1, wherein the chelating composition comprises one or more different structural architectures independently selected from the group consisting of alternating, periodic, diblock, triblock and multiblock and comprise one or more forms independently selected from the group consisting of linear, branched, brush, comb and star.

11. The chelating composition of claim 1, wherein the chelating composition has a lower molecular weight limit of around 1500 Daltons and has no upper molecular weight limit provided it remains soluble in aqueous media prior to the binding of the metal.

12. The chelating composition of claim 1, wherein the essential metal is an essential transition series metal.

13. The chelating composition of claim 1, wherein the essential metal is iron, manganese, copper, cobalt, magnesium or nickel.

14. The chelating composition of claim 1, wherein the living cell or organism is affected in its growth or activities by having insufficient amounts of the essential metal available for its use.

15. A pharmaceutical composition comprising the chelating composition of claim 1 and a pharmaceutically acceptable carrier.

16. A metal binding compound represented by Compound (I),

53

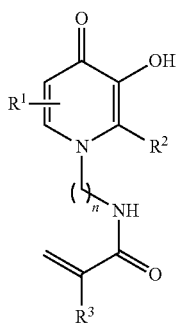

Compound (I)

wherein:
R¹ is independently selected from the group consisting of H, alkyl and alkyl substituted with O, N or S;
R² is independently selected from the group consisting of H, alkyl and alkyl substituted with O, N or S;
R³ is independently selected from the group consisting of H, alkyl and alkyl substituted with O, N or S; and
n is 1 to 12,
wherein Compound (I) is prepared by polymerizing Compound (Ia)

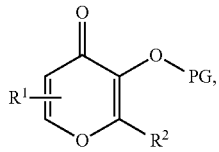

Compound (Ia)

wherein
R¹ is independently selected from the group consisting of H, alkyl and alkyl substituted with O, N or S;
R² is independently selected from the group consisting of H, alkyl and alkyl substituted with O, N or S; and
PG is a protecting group,
with Compound (Ib)

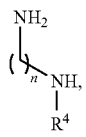

Compound (Ib)

54 wherein
n is 1 to 12; and
R⁴ is COCCH₂R³ or a protecting group,
by a reversible addition-fragmentation chain transfer mechanism with the use of a suitable addition-fragmentation chain transfer agent followed by:
when R⁴ is COCCH₂R³, removing PG to yield Compound (I); or
when R⁴ is a protecting group, removing R⁴, reacting with a suitable acrylate source, and removing PG to yield Compound (I), and
wherein Compound (I) binds one or more essential metal.

17. The metal binding compound of claim 16, wherein
R¹ is H;
R² is methyl;
R³ is methyl; and
n is 1 to 6 or optionally n is at least 2.

18. The chelating composition of claim 1, wherein the first monomer unit is represented by Compound (III)

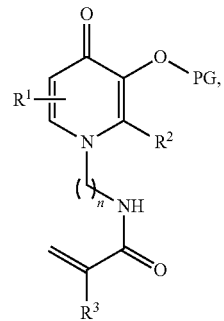

Compound (III)

wherein R¹ is independently selected from the group consisting of H, alkyl and alkyl substituted with O, N or S;
R² is independently selected from the group consisting of H, alkyl and alkyl substituted with O, N or S;
R³ is independently selected from the group consisting of H, alkyl and alkyl substituted with O, N or S;
n is 1 to 12 or optionally n is at least 2; and
PG is a protecting group.

* * * * *